(12) United States Patent
Bally et al.

(10) Patent No.: US 7,789,361 B2
(45) Date of Patent: Sep. 7, 2010

(54) TRANSFER SYSTEM AND TRANSFER DEVICE

(75) Inventors: Alexander Bally, Barrington, RI (US); Eric R. Colburn, Wexford, PA (US); George Gounaris, West Palm Beach, FL (US); Douglas E. Stern, Providence, RI (US)

(73) Assignee: American Sterilizer Company, Mentor, OH (US)

( * ) Notice: Subject to any disclaimer, the term of this patent is extended or adjusted under 35 U.S.C. 154(b) by 940 days.

(21) Appl. No.: 11/429,332

(22) Filed: May 5, 2006

(65) Prior Publication Data

US 2006/0249641 A1 Nov. 9, 2006

Related U.S. Application Data

(60) Provisional application No. 60/678,319, filed on May 6, 2005.

(51) Int. Cl.
*F16M 13/00* (2006.01)
(52) U.S. Cl. ............. 248/229.2; 248/124.2; 248/231.51
(58) Field of Classification Search ............. 248/229.2, 248/229.24, 229.23, 229.14, 229.13, 230.4, 248/230.5, 231.51, 231.61, 229.21, 229.26, 248/124.2
See application file for complete search history.

(56) References Cited

U.S. PATENT DOCUMENTS

| | | | | |
|---|---|---|---|---|
| 1,774,775 A * | 9/1930 | Weitz, Jr. | ................ | 248/229.26 |
| 2,711,300 A | 6/1955 | Nelson | ......................... | 248/214 |
| 2,876,027 A * | 3/1959 | Sulmonetti | .................... | 403/53 |
| 3,385,545 A | 5/1968 | Patton | ....................... | 248/68.1 |
| 3,463,440 A | 8/1969 | Libby, Jr. | .................... | 248/487 |
| 4,572,536 A | 2/1986 | Doughty | ...................... | 280/289 |
| 4,632,221 A * | 12/1986 | Stanford | .................. | 182/186.8 |
| 4,666,111 A | 5/1987 | Schuler | ....................... | 248/125 |
| 4,742,981 A | 5/1988 | Converse | ................. | 248/231.7 |
| 4,795,122 A | 1/1989 | Petre | ........................... | 248/317 |
| 4,832,299 A | 5/1989 | Gorton et al. | ............. | 248/231.7 |
| 4,844,397 A | 7/1989 | Skakoon et al. | .......... | 248/231.7 |
| 4,893,810 A | 1/1990 | Lee | .............................. | 272/123 |
| 4,945,592 A | 8/1990 | Sims et al. | ..................... | 5/508 |
| 5,135,191 A | 8/1992 | Schmuhl | ..................... | 248/125 |
| 5,236,162 A | 8/1993 | Desjardins | .................. | 248/214 |

(Continued)

FOREIGN PATENT DOCUMENTS

DE        9210979         10/1992

(Continued)

*Primary Examiner*—Anita M King
(74) *Attorney, Agent, or Firm*—Kusner & Jaffe; Michael A. Centanni

(57) ABSTRACT

A transfer device for transferring an apparatus from one support to another support. The transfer device is comprised of a housing and two movable clamping elements that are mounted to the housing. Each of the clamping elements is movable between a support-clamping position and a non-clamping, release position. An actuator is in operative engagement with the two clamping elements to move each of the clamping elements between the support-clamping position and the release position. The actuator has a first actuator position wherein one of the clamping elements is in the support-clamping position and another of the clamping elements is in the release position. In a second position, one of the clamping elements is in the release position and the other of the clamping elements is in the support-clamping position.

48 Claims, 15 Drawing Sheets

U.S. PATENT DOCUMENTS

| | | | |
|---|---|---|---|
| 5,306,109 A | 4/1994 | Kreuzer et al. | 414/343 |
| 5,319,816 A | 6/1994 | Ruehl | 5/600 |
| 5,344,169 A | 9/1994 | Pryor et al. | 280/79.3 |
| 5,355,539 A | 10/1994 | Boettger | 5/503.1 |
| 5,358,205 A | 10/1994 | Starkey et al. | 248/225.31 |
| 5,366,191 A | 11/1994 | Bekanich | 248/125 |
| 5,374,074 A | 12/1994 | Smith | 280/304.1 |
| 5,458,305 A | 10/1995 | Woodward | 248/121 |
| 5,482,239 A * | 1/1996 | Smith | 248/229.13 |
| 5,527,125 A | 6/1996 | Kreuzer et al. | 403/325 |
| 5,588,166 A | 12/1996 | Burnett | 5/503.1 |
| 5,655,741 A | 8/1997 | Watkins | 248/289.11 |
| 5,728,077 A | 3/1998 | Williams et al. | 604/246 |
| 5,779,207 A | 7/1998 | Danby | 248/230.4 |
| 5,797,568 A | 8/1998 | Gongora et al. | 248/122.1 |
| 5,898,961 A | 5/1999 | Ambach et al. | 5/600 |
| 5,987,670 A | 11/1999 | Sims et al. | 5/600 |
| 6,073,285 A | 6/2000 | Ambach et al. | 5/600 |
| 6,079,678 A | 6/2000 | Schott et al. | 248/229.15 |
| 6,179,260 B1 | 1/2001 | Ohanian | 248/229.16 |
| 6,382,576 B1 | 5/2002 | Heimbrock | 248/227.3 |
| 6,585,206 B2 | 7/2003 | Metz et al. | 248/229.1 |
| 6,725,483 B2 | 4/2004 | Gallant et al. | 5/658 |
| 6,786,302 B2 * | 9/2004 | Liew et al. | 182/186.8 |
| 6,966,086 B2 | 11/2005 | Metz et al. | 5/510 |
| 6,969,031 B2 | 11/2005 | Ugent et al. | 248/125.8 |
| 7,090,181 B2 * | 8/2006 | Biba et al. | 248/288.31 |
| 2004/0104321 A1 | 6/2004 | Marsolais et al. | 248/229.1 |
| 2005/0000019 A1 | 1/2005 | Newkirk et al. | 5/600 |
| 2005/0253034 A1 | 11/2005 | Bally et al. | 248/276.1 |
| 2006/0038098 A1 | 2/2006 | Metz et al. | 248/229.1 |
| 2006/0179571 A1 | 8/2006 | Newkirk | 5/600 |

FOREIGN PATENT DOCUMENTS

WO    WO 2005/037163 A2    4/2005

* cited by examiner

TRANSFER SYSTEM AND TRANSFER DEVICE

This application claims the benefit of U.S. Provisional Application No. 60/678,319, filed on May 06, 2005.

FIELD OF THE INVENTION

The present invention relates generally to transfer systems and, more specifically, to a transfer device and transfer system for supporting and transporting one or more apparatus.

BACKGROUND OF THE INVENTION

The present invention is particularly applicable in supporting and transporting medical devices used in the care of a patient, and shall be described with particular reference thereto. However, it will be appreciated that the present invention may find advantageous application in supporting and transporting other types of objects in other applications.

In modern hospitals and medical facilities, a great deal of medical equipment is used in the care and treatment of patients. It is quite common for a patient to be connected to a number of different medical devices, such as pumps for administrating intravenous (IV) fluids, monitors, oxygen tanks, electrical strips and the like. Typically, these medical devices are mounted onto a vertical pole, conventionally referred to as an "IV pole." It has been known to support IV poles on a wheeled base that can be positioned adjacent a hospital bed or can be transported with the bed to another location.

In recent years, the number and size of medical devices routinely attached to a patient has increased, thus requiring more sturdy structures for supporting such equipment. For these and other reasons, it is necessary that a support or pole, and the associated medical devices attached thereto, be firmly supported near a patient. In this respect, mounting a support pole and its associated devices to a rigid, stationary surface, such as a wall or ceiling, is becoming preferable because it provides better structural support for the pole.

At the same time, it is often necessary to transport a patient, together with the medical devices that are operatively connected to the patient, to another location in the hospital for medical procedures or testing. At these times, it is necessary that the support pole and medical devices be easily transferred from the wall or ceiling support to a hospital bed, or to some other type of patient-transfer vehicle, for movement to another location.

The present invention provides a support and transfer device for supporting and transporting one or more medical devices between a wall or ceiling support and a patient-transfer vehicle, which system provides positive transfer from one to another, and vice-a-versa.

SUMMARY OF THE INVENTION

In accordance with a preferred embodiment of the present invention, there is provided a transfer device transferable from one support to another support. The transfer device is comprised of a housing having first and second support-receiving recesses. Each recess is dimensioned to receive a support therein. A first clamping element is mounted to the housing. The first clamping element is associated with the first recess and is movable relative thereto between a support-clamping position wherein the first clamping element captures the support in the first recess and a release position wherein the support is movable into and out of the first recess. A second clamping element is mounted to the housing. The second clamping element is associated with the second recess and is movable relative thereto between a support-clamping position wherein the jaw captures the support in the second recess and a release position wherein the support is movable into and out of the second recess.

In accordance with another aspect of the present invention, there is provided a device transferable between one support and another support. The device is comprised of a housing. First and second movable clamping elements are mounted to the housing, wherein each of the clamping elements is movable between a support-clamping position and a support-release position. A movable actuator is connected to the first and second clamping elements. The actuator is movable between a first actuator position and a second actuator position and operable to move each of the clamping elements between the support-clamping position and the support-release position. A locking element is connected to the actuator. The locking element has a first position that prevents movement of the actuator. A second position allows limited movement of the actuator between the first and second actuator positions. A third position allows full movement of the actuator between the first and second actuator positions.

In accordance with another aspect of the present invention, there is provided a transfer device for transferring an apparatus from one support to another support. The transfer device is comprised of a housing. Two movable clamping elements are mounted to the housing. Each of the clamping elements is movable between a support-clamping position and a non-clamping, release position. An actuator is in operative engagement with the two clamping elements to move each of the clamping elements between the support-clamping position and the release position. The actuator has a first actuator position wherein one of the clamping elements is in the support-clamping position and another of the clamping elements is in the release position. In a second position, one of the clamping elements is in the release position and the other of the clamping elements is in the support-clamping position.

In accordance with another aspect of the present invention, there is provided a transfer system comprised of a plurality of supports, each of the supports having areas of like cross-sectional shapes. A device is alternately attachable to one of the supports. The device has two jaws that are each movable between a support clamping position, wherein a jaw captures a support in the device and a release, non-clamping position. One of the jaws is in the clamping position attaching the device to one of the plurality of supports when the other of the jaws is in a non-clamping position.

In accordance with yet another aspect of the present invention, there is provided a device that is transferable between two like supports, comprising two clamping elements each movable between a support-clamping position. The clamping element attaches the device onto a support and a non-clamping position, wherein the clamping element releases the device from a support. A means is provided for moving one of the two clamping elements to the non-clamping position after another of the two clamping elements is moved to the clamping position.

In accordance with still another aspect of the present invention, there is provided a method of moving a patient care apparatus between supports, comprising the steps of:

providing a transfer device mounted to a first support, the transfer device supporting a patient care apparatus and having first and second clamping elements that are each movable between a support-clamping position and a support-release position, one of the clamping elements being in the clamping position attaching the transfer device to the first support and the other of the clamping elements being in the support-release position;

aligning a second support relative to the other of the clamping elements;

moving the other of the clamping elements to the support-clamping position attaching the transfer device to the second support; and moving the one of the clamping elements to the support-release position once the other of the clamping elements is in the support-clamping position attaching the transfer device to the second support.

An advantage of the present invention is a transfer system and device that allows transfer of apparatus between one support and another support.

An advantage of the present invention is a transfer system and device that allows transfer of apparatus between a stationary support and a transport vehicle, and vice-a-versa.

Another advantage of the present invention is a transfer system and device that allows transfer of medical apparatus between a stationary support and a patient-transport vehicle, and vice-a-versa.

Another advantage of the present invention is a transfer system and device that allows transfer of an IV pole, having one or more medical devices mounted thereon, between a stationary support and a support on a patient-transfer vehicle.

Another advantage of the present invention is a transfer system and device that insures positive transfer of an IV pole and the attendant apparatus from a stationary support to a support on a patient-transfer vehicle, and vice-a-versa, or between supports on two patient-transfer vehicles.

A still further advantage of the present invention is a transfer system and device as described above that is attachable to either a support on a stationary support or a support on a patient-transfer vehicle.

Another advantage of the present invention is a transfer system and device wherein a patient, and medical equipment operatively attached to the patient, can be quickly transferred from one location within a hospital to another.

Another advantage of the present invention is a transfer system and device as described above that transfers medical devices from one support to another support, without requiring vertical adjustment or repositioning.

Another advantage of the present invention is a transfer system and device capable of supporting and transferring apparatus, transversely from one support to another support.

Another advantage of the present invention is a transfer system and device wherein medical apparatus can be transferred from one support to another support.

A still further advantage of the present invention is a transfer system and device as described above, wherein the medical apparatus remain at the same height, i.e., elevation, while being transferred from one support to another support.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
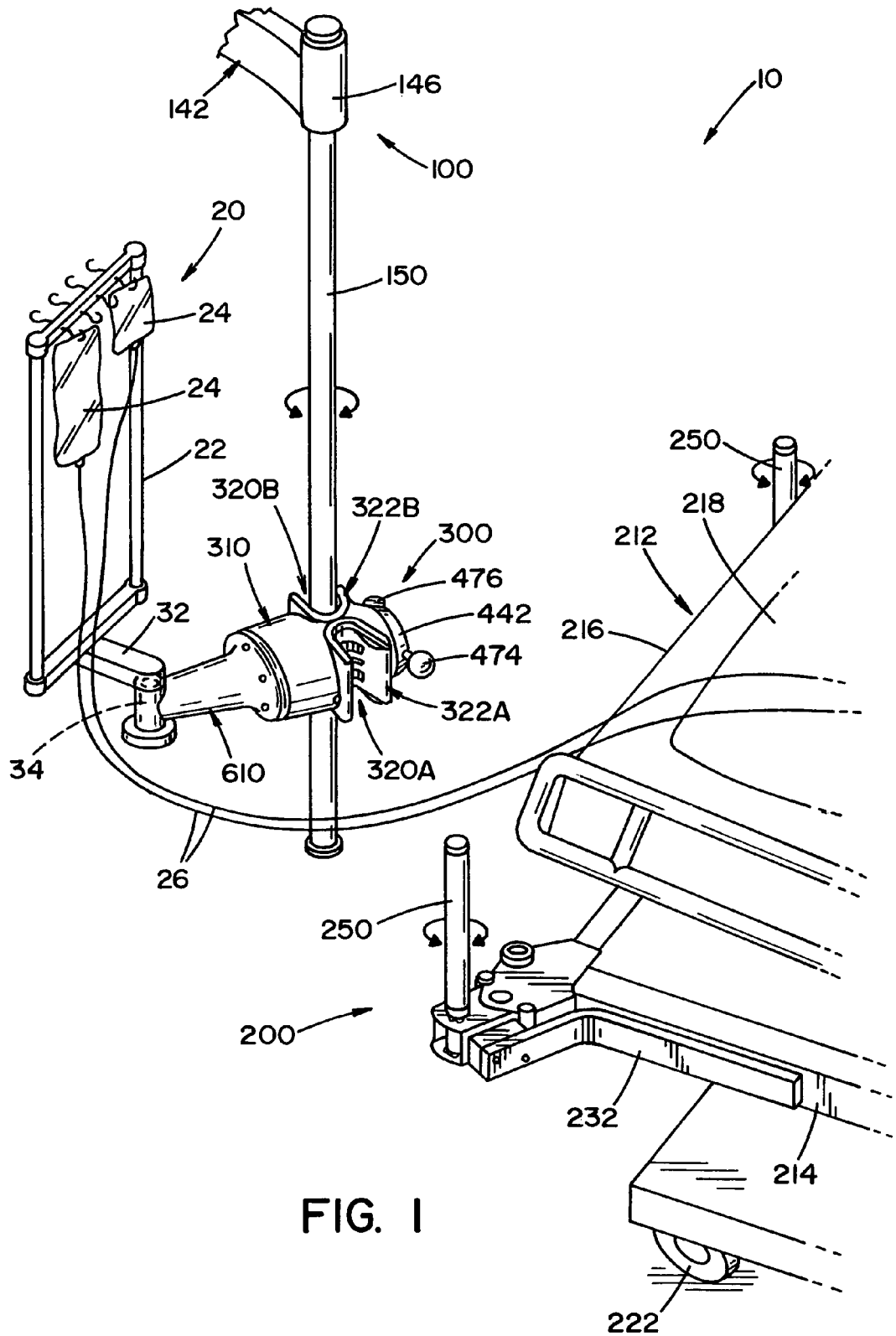
FIG. 1 is a perspective view of a transfer system and device according to a preferred embodiment of the present invention, showing the transfer device supporting a rack for medical devices.

Referring now to the drawings, wherein the showings are for the purpose of illustrating a preferred embodiment of the invention only and not for the purpose of limiting same, FIG. 1 is a perspective view, showing a transfer system 10 for supporting apparatus. Transfer system 10 is particularly applicable to supporting and transporting medical apparatus 20 in a medical facility and will be described with particular reference thereto. However, as will be appreciated from a further reading of the specification, transfer system 10 may find advantageous application in supporting and moving other objects in other settings.

Transfer system 10 is comprised of a stationary support assembly 100, a vehicle-support assembly 200 and a transfer device 300 that supports patient-care apparatus 20 and is capable of transferring patient-care apparatus 20 between stationary support assembly 100 and a vehicle-support assembly 200, and vice-a-versa.

As used herein, the term "stationary support assembly" refers to a support assembly that is affixed to any permanent, rigid structure, such as, by way of example and not limitation, a wall support, a patient headwall, a ceiling support, or a stationary structural support.

The term "vehicle-support assembly" refers to a support assembly that is affixed to any type of medical structure that can support patients and transfer such patients from one location to another, such as, by way of example and not limitation, a hospital bed, a hospital stretcher, cribs, a surgical chair or a wheel chair.

The term "patient-care apparatus" refers to any type of medical apparatus used in the care of a patient, such as, by way of example and not limitation, IV bags, pumps, or monitors.

Figure 1A:
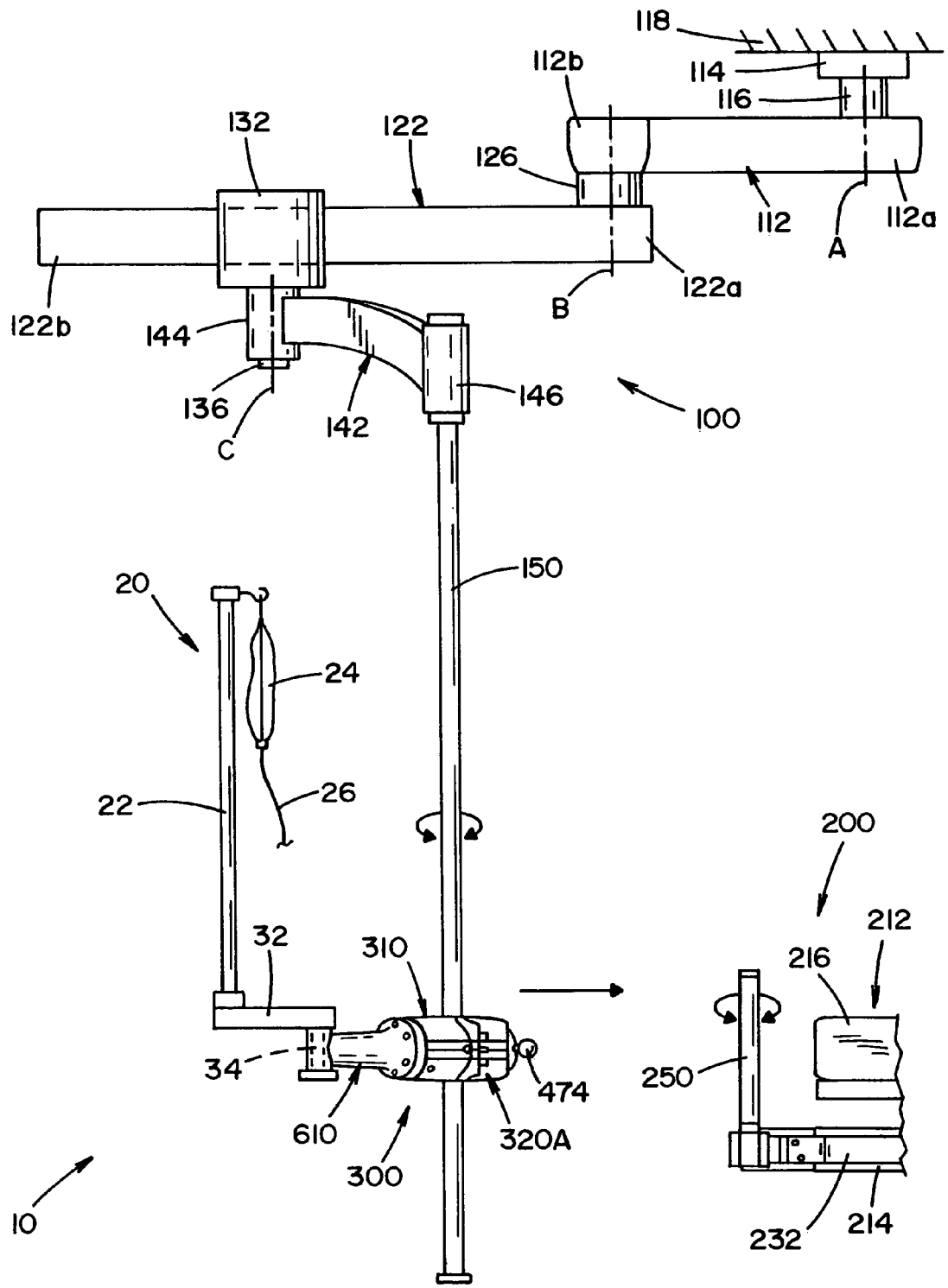
FIG. 1A is a side, elevational view of the transfer system and device shown in FIG. 1, showing the transfer device about to engage a support on a patient-transfer vehicle.
Figure 2:
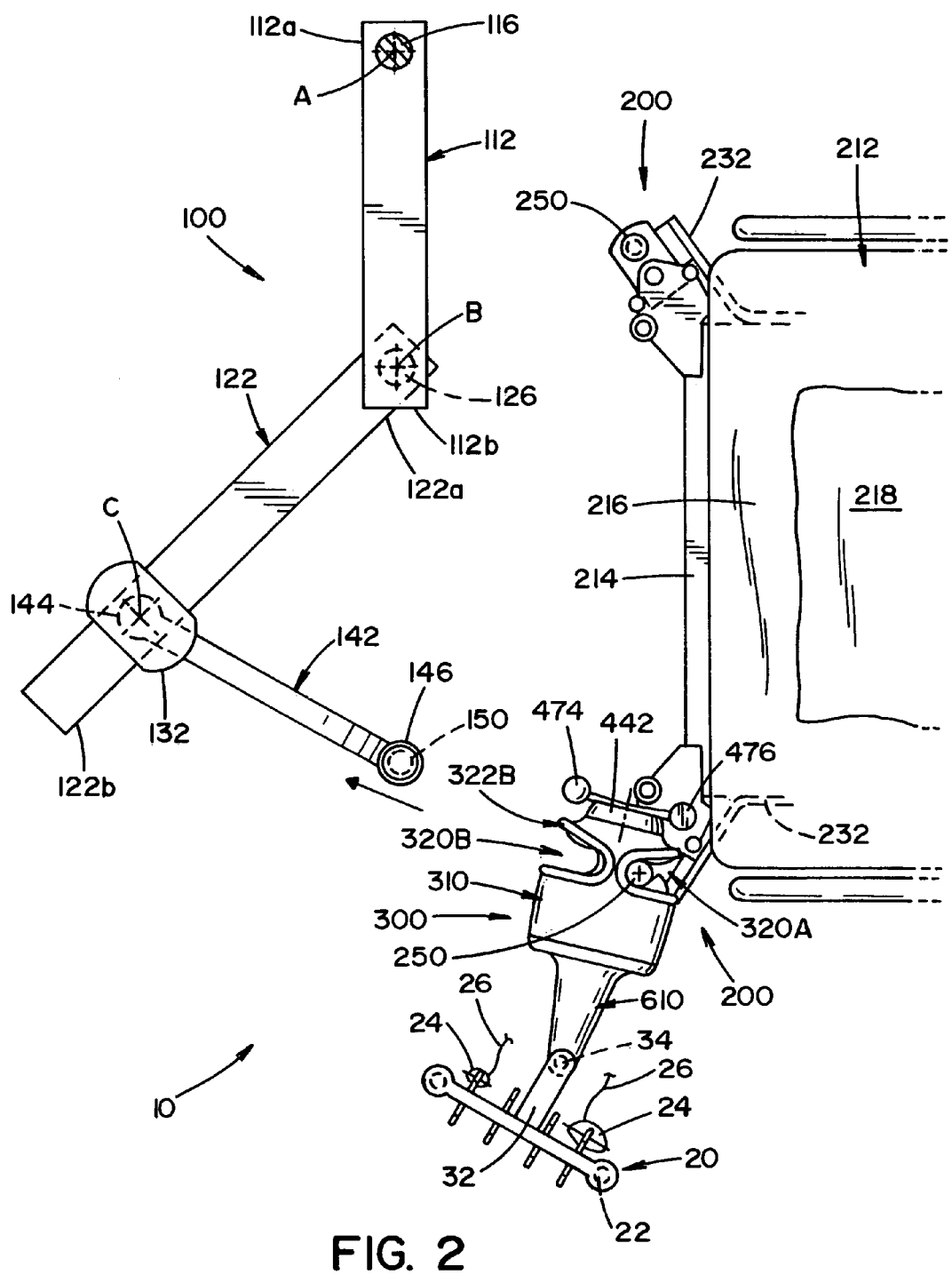
FIG. 2 is a top plan view of the transfer device, showing the transfer device immediately after the transfer device has been transferred from the wall support to a support on a patient-transfer vehicle.

In the embodiment shown, stationary support assembly 100, best seen in FIG. 1A, is comprised of a first arm section 112, a second arm section 122, and a support arm 142. First arm section 112 is an elongated member having a first end 112a and a second end 112b. First end 112a of first arm section 112 is connected to a ceiling mount 114 by a first pivot pin 116. Mount 114 is attached to a ceiling surface 118 by means not shown. First arm section 112 is mounted to pivot pin 116 to be movable in a horizontal plane about a first vertical axis "A" through pivot pin 116.

Second arm section 122 has a first end 122a and a second, free, end 122b. Second end 112b of first arm section 112 is pivotally connected to first end 122a of second arm section 122 by a second pivot pin 126 that defines a second vertical axis "B." Second end 122b of arm section 122 is free to move in a horizontal plane about second vertical axis "B" that extends through second pivot pin 126 and is parallel to axis "A."

A collar 132 is attached to second arm section 122. Collar 132 is movable, i.e., repositionable, along second arm section 122. Collar 132 has a downward-extending pin 136 that defines third vertical axis "C" and is parallel to axes "A" and "B."

As best seen in FIG. 1A, support arm 142 has a slight, downward curvature. One end of support arm 142 includes a first sleeve 144 that is attached to the downward-extending pin. A second sleeve 146 is formed at the free end of support arm 142. Support arm 142 is rotatable about third vertical axis "C." First and second arm sections 112, 122 define an articulating arm assembly that, in the embodiment shown, is attached to ceiling mount 114 to define stationary support assembly 100. A support 150 extends from sleeve 146. While support 150 may assume a number of different configurations, support 150 is preferably an elongated structure that extends along an axis and has a uniform cross-sectional shape along such axis. In the embodiment shown, support 150 is a cylindrical, metal pipe. It is contemplated that support 150 may be comprised of other materials and/or shapes. By way of example and not limitation, support 150 may have a rectangular or oval cross-section, and/or may be formed of other metals, polymers or reinforced polymers, such as a carbon-reinforced polymer. Support 150 is preferably mounted within sleeve 146 to extend vertically from sleeve 146 and be rotatable about its own axis, as illustrated by an arrow in FIG. 1.

Vehicle-support assembly 200 is attached to a medical structure for transporting patients. In the embodiment shown, the medical structure is a hospital bed 212, partially shown in FIG. 1, having a lower frame 214 that supports a mattress 216 and pillow 218. As illustrated in the drawings, lower frame 214 of hospital bed 212 is supported on casters 222, such that hospital bed 212 is movable. Bracket 232 is mounted to frame 214 of hospital bed 212. Bracket 232 is preferably mounted to hospital bed 212 by fasteners (now shown). Bracket 232 is designed to support a second, vertical support 250. Bracket 232 may be mounted to each corner of hospital bed 212 to support a support 250 at each corner of bed 212. Support 250 has essentially the same cross-sectional shape as support 150. In the embodiment shown, support 250 is also cylindrical in shape and extends upward from the bracket in a vertical direction. Support 250 is preferably mounted to bracket 232, such support is rotatable about its own vertical axis, as illustrated by an arrow in FIG. 1.

As will be better understood from further reading of the present application, both supports 150, 250 preferably have essentially identical cross-sectional shapes.

In the embodiment shown, patient-care apparatus 20 is comprised of a rack 22 supporting conventional intravenous (IV) solution bags 24, having tubes 26 extending therefrom to a patient (not shown) on hospital bed 212. Rack 22 is attached to a lateral arm 32 that is, in turn, mounted to a post 34. Post 34 is designed to attach to transfer device 300, as shall be described in greater detail below. As will be appreciated from a further reading of the specification, it is contemplated that transfer device 300 may be used to support and transfer other types of patient-care apparatus 20.

As indicated above, transfer device 300 is dimensioned to support the medical apparatus 20, and, in turn, transfer device 300 is dimensioned to be supported by either support 150 of stationary support assembly 100 or support 250 of vehicle-support assembly 200. In this respect, in accordance with one aspect of the present invention, transfer device 300 is adapted to be affixed, i.e., to be attached, to support 150 or 250. In accordance with another aspect of the present invention, transfer device 300 is adapted to be transferred from one support 150 or 250 to another support 150 or 250, while medical apparatus 20 are attached to transfer device 300.

Figure 3:
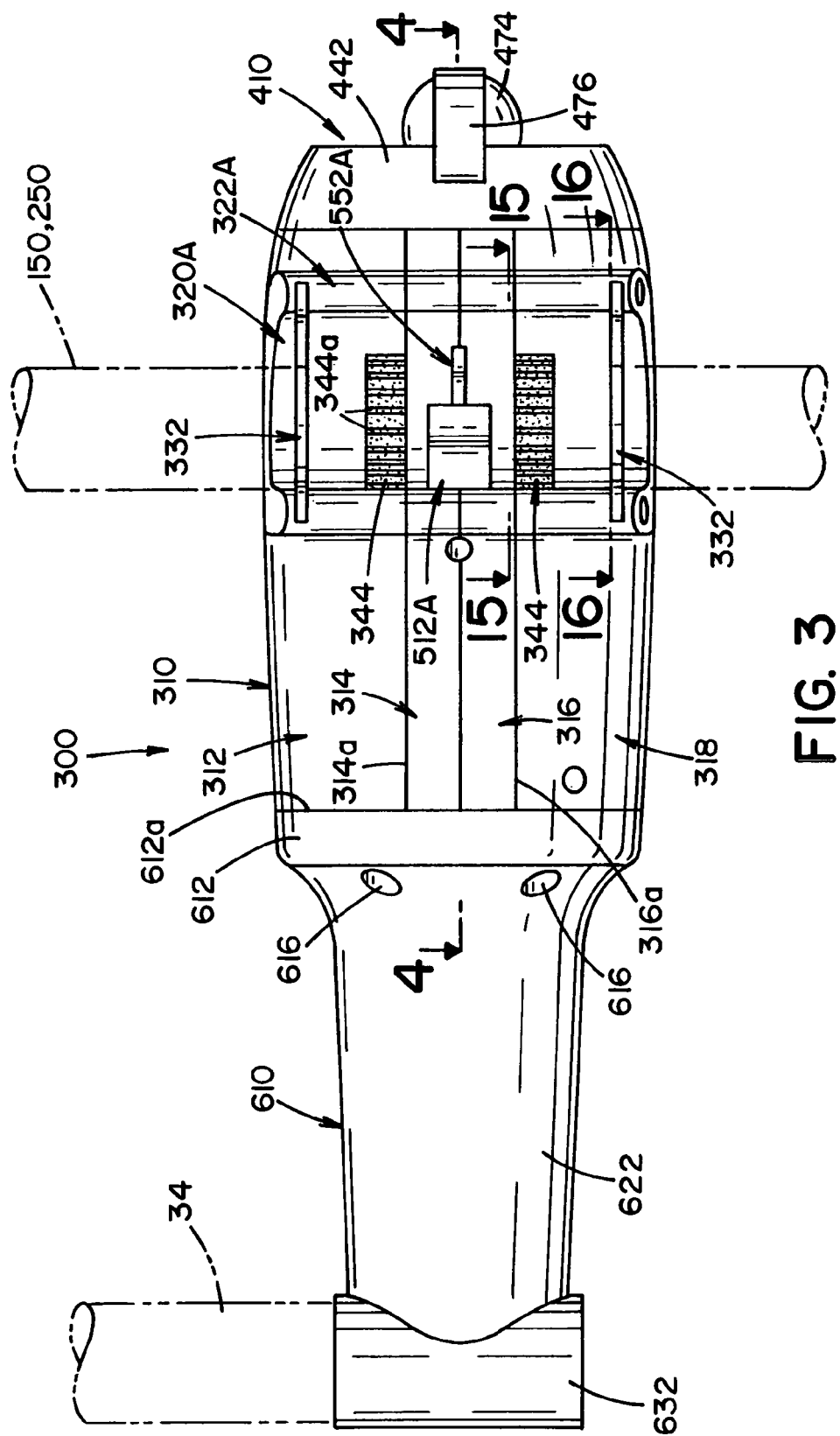
FIG. 3 is an enlarged, side elevational view of the transfer device shown in FIG. 1.

Transfer device 300, best seen in FIGS. 3, 4-8, and 17, is generally comprised of a body section 310 and an outward-extending adapter section 610. Body section 310 is comprised of an upper housing 312, inner plates 314, 316, and a lower housing 318. Upper housing section 312, inner plates 314, 316, and lower housing 318 are dimensioned to be attached together, as best seen in FIG. 3, with inner plates 314, 316 captured between housings 312, 318. A handle/actuator assembly 410 (best seen in FIG. 13) and a pair of jaw/latch assemblies 510A, 510B (510B best seen in FIG. 14) are dimensioned to be captured within body section 310, between inner plates 314, 316.

Figure 4:
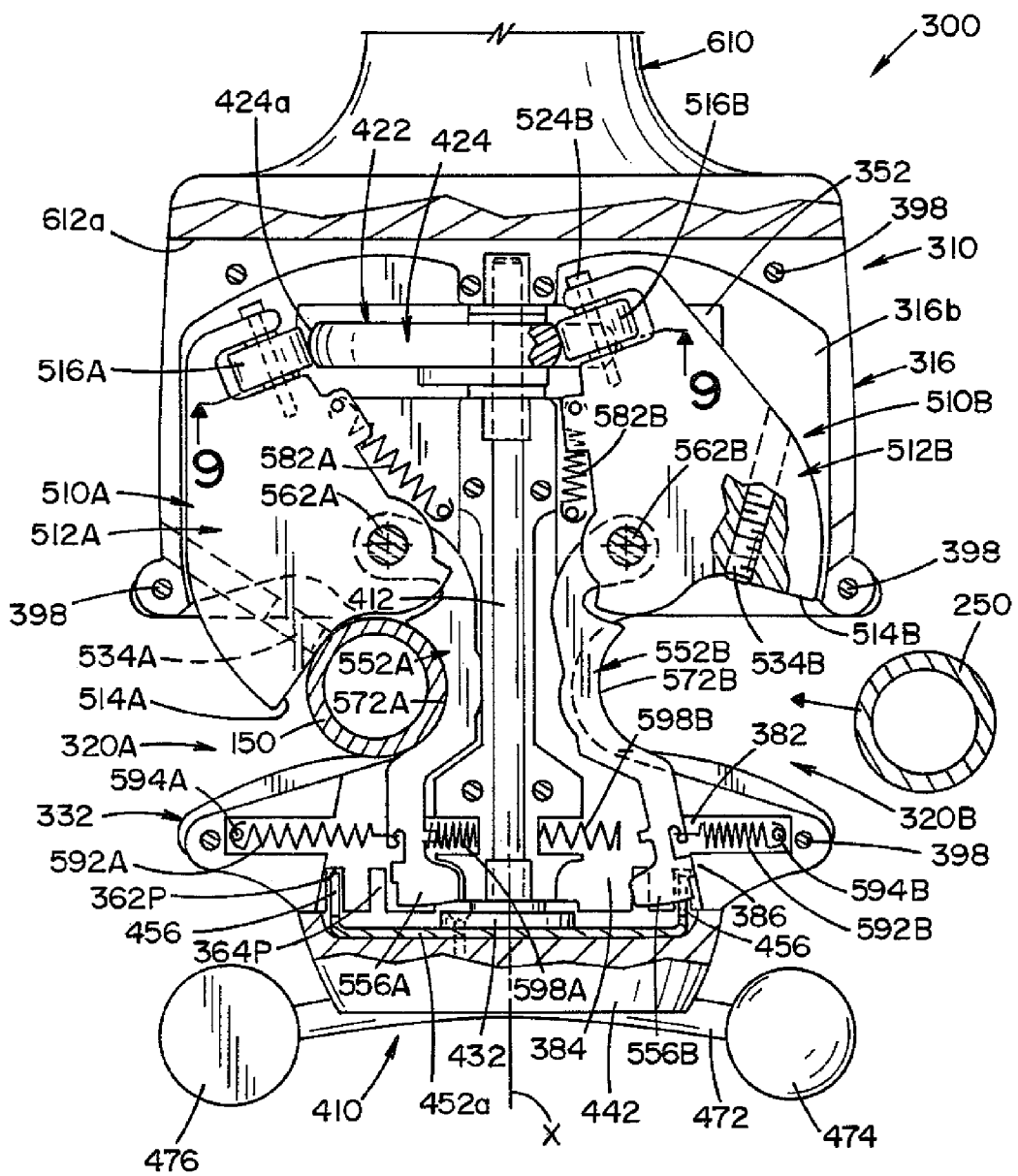
FIG. 4 is a sectional view taken along lines 4-4 of FIG. 3, showing the transfer device attached to a first support and about to receive a second support.

When housings 312, 318 and associated inner plates 314, 316 are assembled together with the handle/actuator assembly 410 and jaw/latch assemblies 510A, 510B disposed therebetween, body section 310 defines two opposite-facing, support-receiving recesses or openings 320A, 320B, best seen in FIG. 4. Support-receiving recesses 320A, 320B are dimensioned to receive a support 150 or 250, such that transfer device 300 may be affixed to support 150, 250, as shall be described in greater detail below.

As best seen in FIG. 1, upper and lower housing 312, 318 and inner plates 314, 316 are formed such that, when assembled, body section 310 includes generally U-shaped collar portions 322A, 322B that define the edges of support-receiving recesses 320A, 320B. Collars 322A, 322B extend outward from body section 310 to define generally U-shaped, support-receiving recesses 320A, 320B.

Figure 16A:
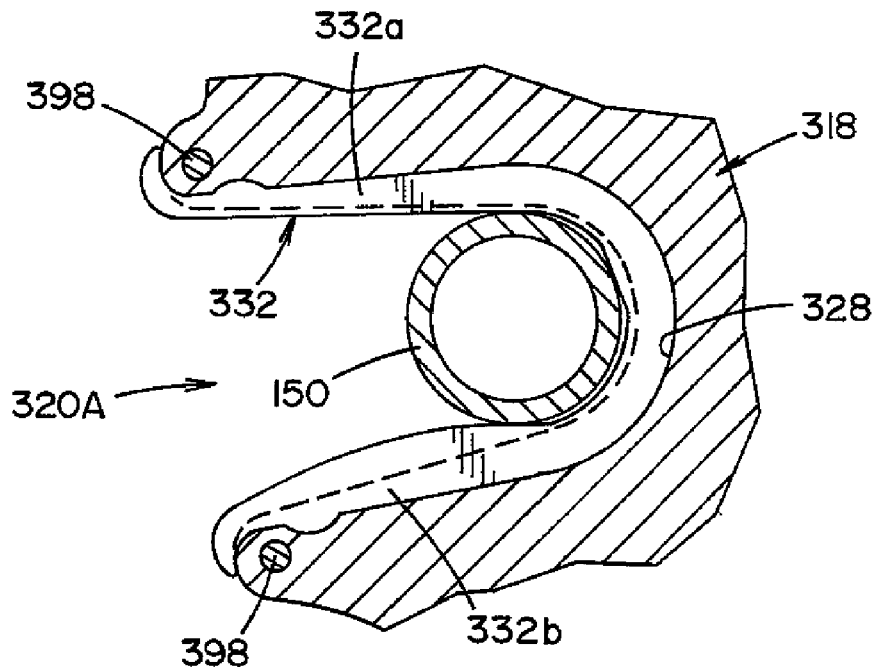
FIG. 16A is a sectional view taken along lines 16-16 of FIG. 3, showing a support relative to a guide within a support-receiving recess.
Figure 16B:
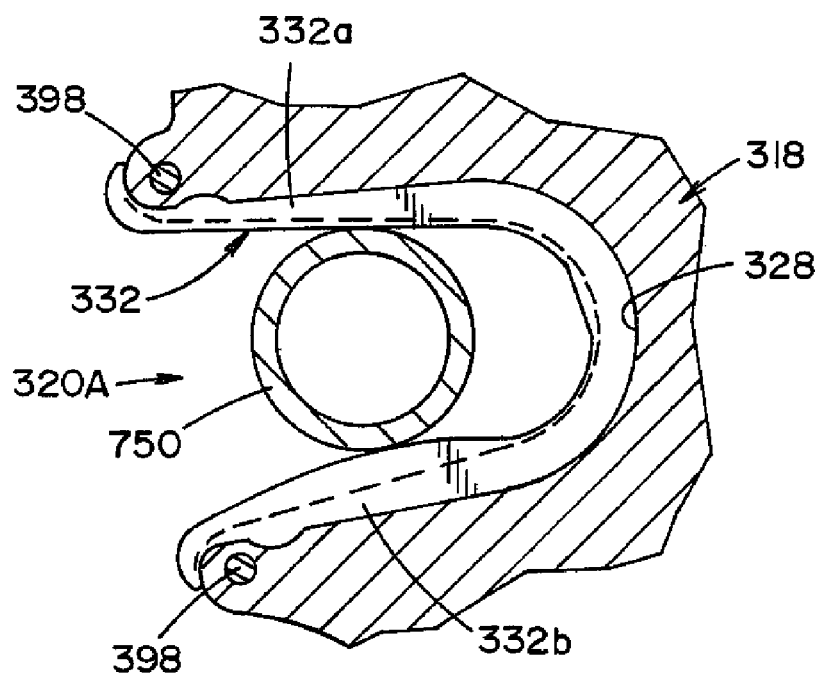
FIG. 16B is a sectional view of the guide and support-receiving recess of FIG. 16A, showing an oversized support relative thereto.
Figure 17:
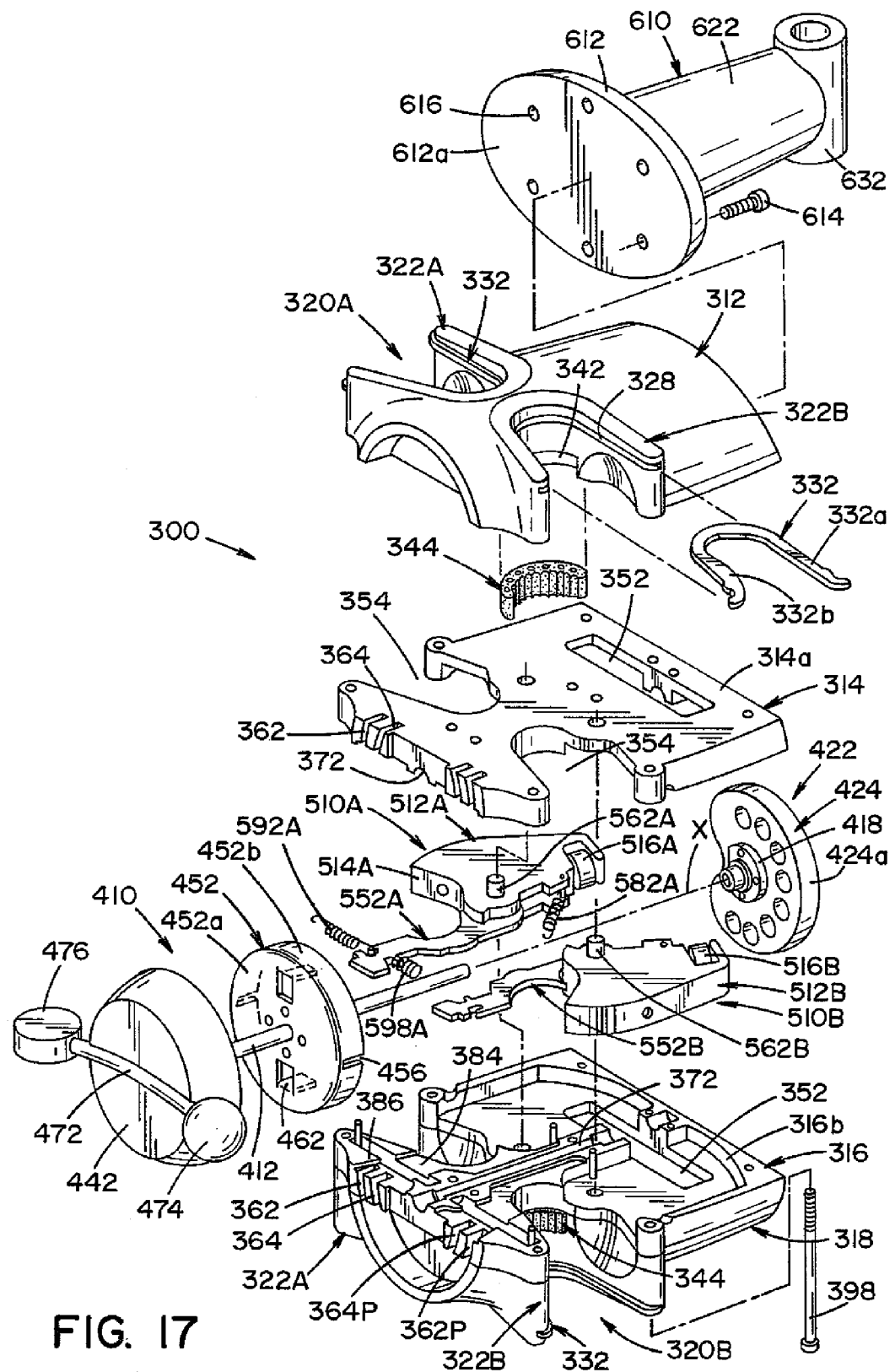
FIG. 17 is an exploded view of the transfer device.

Housings 312, 318 include outward-extending areas that essentially define U-shaped collars 322A, 322B of the body section 310. As best seen in FIG. 17, a slot 328 is formed along the inner surface of each collar 322A, 322B near the edge thereof. Slot 328 is dimensioned to receive a U-shaped guide 332, best seen in FIG. 16.

Figure 15:
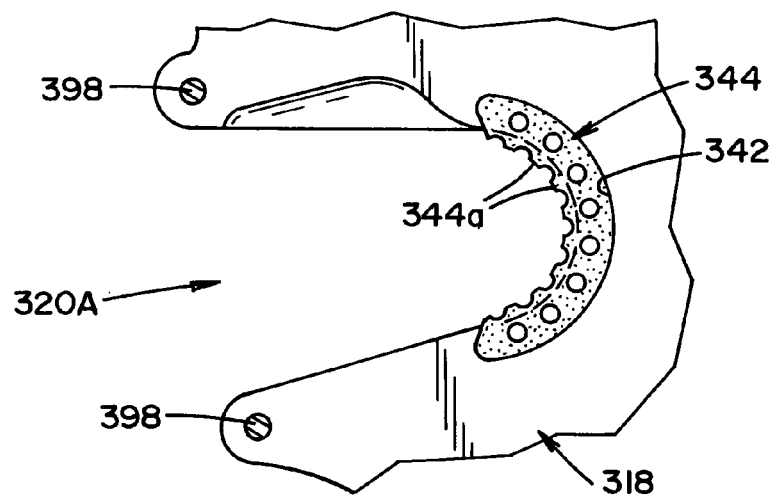
FIG. 15 is a sectional view taken along lines 15-15 of FIG. 3.

A cavity 342, best seen in FIG. 17, is formed within each support-receiving recess 320A, 320B in housings 312, 318. Cavity 342 is formed along the inner edge of each support-receiving recess 320A, 320B and is dimensioned to receive pad 344, best seen in FIGS. 15 and 17. In the embodiment shown, each pad 344 is generally U-shaped and includes spaced-apart ribs 344a along one side thereof. Pads 344 are preferably formed of a tough, resilient polymer and are dimensioned to be captured within cavities 342 in housings 312, 318, with ribs 344a thereon extending along the inner surface of support-receiving recess 320A, 320B in body section 310, as shown in FIG. 3.

Inner plates 314, 316 are essentially identical. Each inner plate 314, 316 includes a flat planar, outer surface 314a, 316a and a contoured, inner surface 314b, 316b. Outer surfaces 314a, 316a face outward from the center of body section 310 when the inner plates 314, 316 are assembled with upper and lower housings 312, 318. In other words, outer surfaces 314a, 316a of inner plates 314, 316 face and engage upper housing 312 and lower housing 318, respectively. Contoured inner surfaces 314b, 316b are formed to receive handle/actuator assembly 410 and jaw/latch assemblies 510A, 510B.

In FIG. 17, outer surface 314a of inner plate 314, which is disposed against upper housing 312, is shown, and contoured surface 316b of inner plate 316, that is disposed against lower housing 318 is shown. Each inner plate 314, 316 includes an elongated, rectangular slot 352 at one end thereof and two outward-extending notches or openings 354 in the sides thereof that define a portion of support-receiving recesses 320A, 320B.

Slots 362, 364, best seen in FIG. 17, are formed in the front end face of each inner plate 314, 316. Slots 362, 364 are rectangular in shape and extend along circular paths that are symmetrical about a central axis, designated "X" in FIG. 17. As shall be described in greater detail below, when inner plates 314, 316 are assembled together, slots 362, 364 in the respective inner plates 314, 316, align and define, respectively, an inner circular passage, designated 362P, and an outer circular passage, designated 364P, through the front end faces of inner plates 314, 316.

Figure 12:
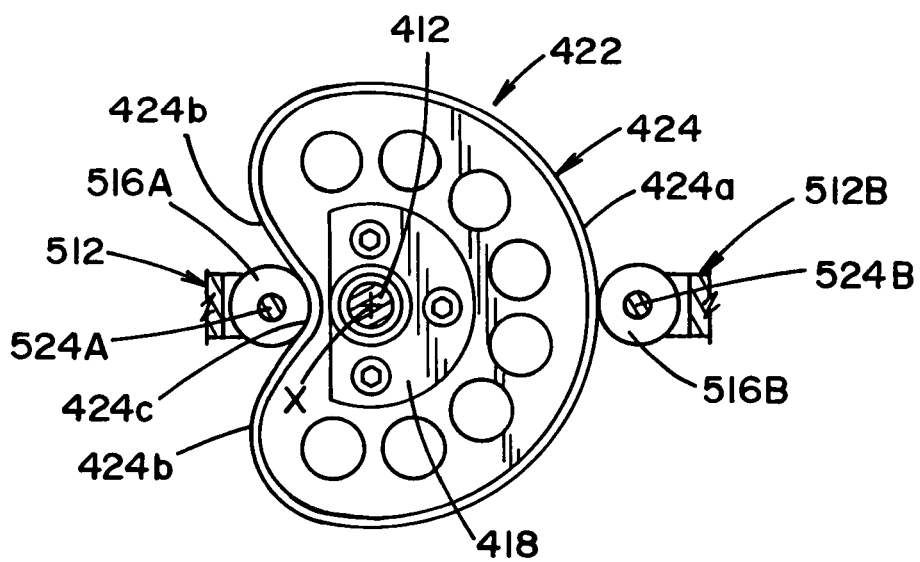
FIG. 12 is a sectional view taken along lines 12-12 of FIG. 8.
Figure 13:
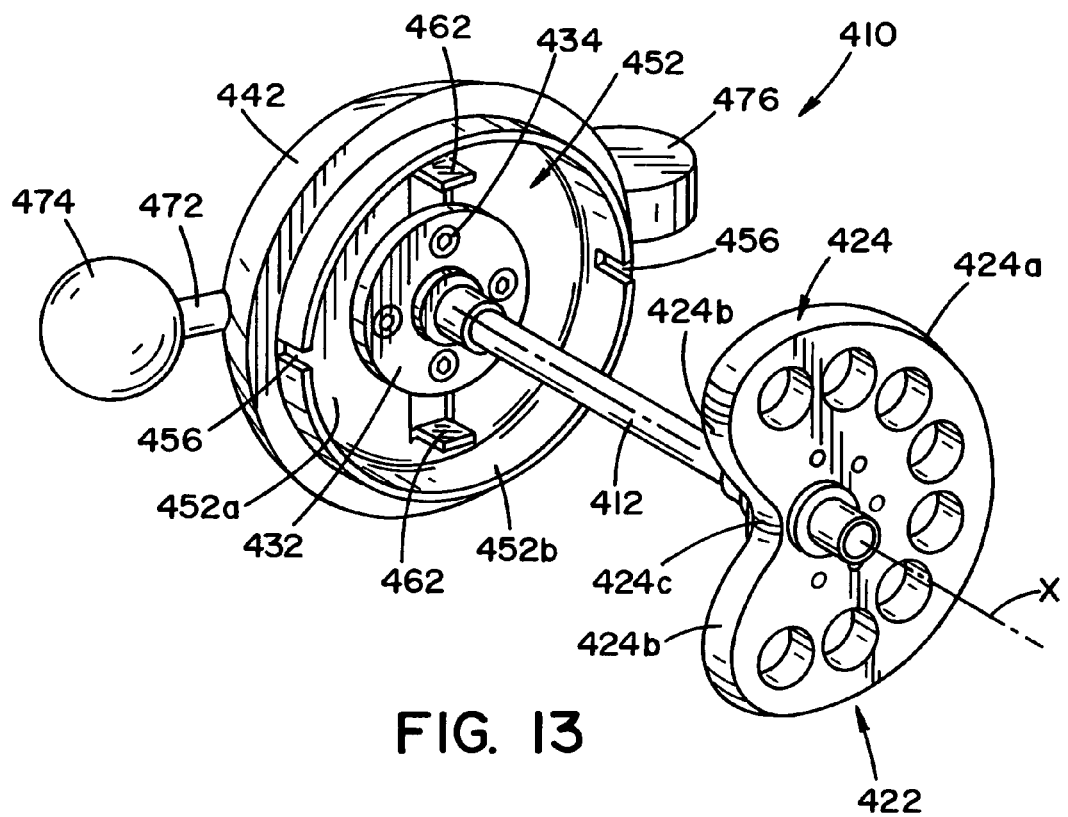
FIG. 13 is a perspective view of a control-handle assembly.

Referring now to FIG. 13, handle/actuator assembly 410 is best seen. Handle/actuator assembly 410 includes an elongated shaft 412. An actuator 422 is mounted at one end of shaft 412. Actuator 422 is attached to a flanged sleeve 418, best seen in FIGS. 9-12, that, in turn, is attached to shaft 412. In the embodiment shown, actuator 422 is a cam element. The cam element is generally kidney-shaped and, as best seen in FIGS. 9-12, defines a cam surface 424 having a circular section 424a that defines the major portion of the cam surface. In the embodiment shown, circular section 424a of cam surface 424 extends radially about shaft 412 for over 180 angular degrees. Cam surface 424 also includes transition sections 424b. Transition sections 424b are formed at opposite ends of circular section 424a and converge toward a valley section 424c.

A second flanged sleeve 432, best seen in FIG. 13, is disposed at the other end of shaft 412. An end-cap 442 is mounted to the flange portion of second flanged sleeve 432 by fasteners 434 extending through second flanged sleeve 432 into cap 442. An intermediate plate 452 is captured between cap 442 and the flanged portion of second flanged sleeve 432. Intermediate plate 452 includes a circular disc portion 452a and a cylindrical wall portion 452b extending to one side of disc portion 452a. In the embodiment shown, intermediate plate 452 is disposed such that cylindrical wall portion 452b extends toward actuator 422. Cylindrical wall portion 452b is symmetrical about the axis of shaft 412. Opposing slots 456 are formed in cylindrical wall 452b, as best seen in FIG. 13. A pair of spaced-apart tabs 462 extends from the surface of intermediate plate 452 toward actuator 422. Tabs 462 are symmetrically spaced on opposite sides of the axis of shaft 412 and are disposed within cylindrical wall 452b, i.e., between cylindrical wall 452b and the axis of shaft 412. A handlebar 472 is attached to and traverses the end face of end-cap 442. Handlebar 472 is dimensioned to extend beyond end-cap 442. Grips are mounted at the distal ends of handle bar 472. In the embodiment shown, grip 474 is spherical in shape and grip 476 has the shape of a cylindrical disc.

Handle/actuator assembly 410 is dimensioned to be captured between inner plates 314, 316. An elongated, cylindrical groove 372, best seen in FIG. 17, is formed in contoured surface 314b, 316b of inner plates 314, 316 such that, when inner plates 314, 316 are assembled together, a cylindrical passage, that is dimensioned to receive shaft 412, is formed. Handle/actuator assembly 410 and inner plates 314, 316 are dimensioned such that, when shaft 412 is captured within cylindrical groove 372 in inner plates 314, 316, actuator 422 is positioned and extends through rectangular slot 352 in inner plates 314, 316.

As best seen in FIGS. 4-8, when handle/actuator assembly 410 is captured between inner plates 314, 316, cylindrical wall portion 452b of intermediate plate 452 is disposed within slots 362 that define outer circular passage 362P in the end faces of inner plates 314, 316, and tabs 462 are positioned to be movable within (through) circular passage 364P defined by slots 364 in the end faces of inner plates 314, 316.

Inner plates 314, 316 are also designed to capture jaw/latch assemblies 510A, 510B therebetween. Jaw/latch assemblies 510A, 510B are essentially identical, and, therefore, only jaw/latch assembly 510B shall be described in detail, it being understood that such description applies equally to jaw/latch assembly 510A. In the description of jaw/latch assembly 510B, components shall be described by a reference number and the suffix "B." In the drawings, like components of jaw/latch assembly 510A bear the same reference number with the suffix "A."

Figure 14:
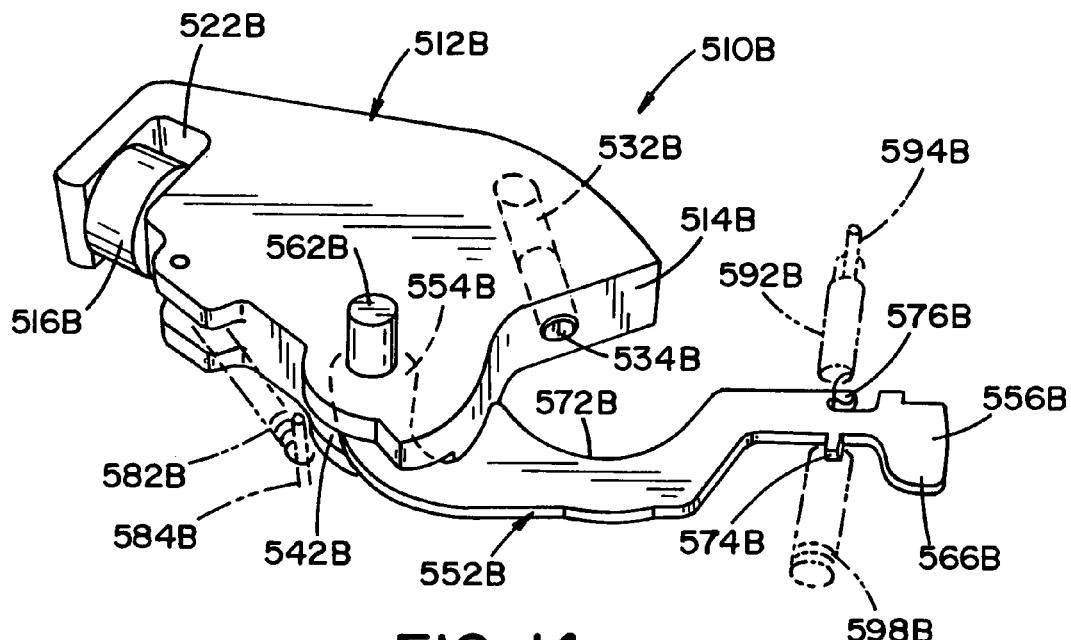
FIG. 14 is a perspective view of a jaw/latch assembly.

Referring now to FIG. 14, jaw/latch assembly 510B is best seen. Jaw/latch assembly 510B is comprised of a jaw element 512B and a latch element 552B. A jaw face 514B is formed along one edge of jaw element 512B. A cam follower 516B is mounted to the other end of jaw element 512B. In the embodiment shown, cam follower 516B is a roller that is mounted within a notch 522B in the end of jaw element 512B. Roller 516B is mounted to a pin 524B, best seen in FIGS. 4-8, extending into jaw element 512B through notch 522B. A cylindrical bore 532B extends through jaw element 512B and communicates with jaw face 514B. Bore 532B includes internal threads to receive an adjusting screw 534B. In the embodiment shown, jaw element 512B is formed from a relatively thick plate material, wherein jaw element 512B has planar upper and lower surfaces. A thin slot 542B is formed within one edge of the jaw element 512B. Slot 542B is co-planar with, and disposed between, the planar surfaces of jaw element 512B.

Latch element 552B is an elongated structure, having a first end 554B and a second end 556B. First end 554B is dimensioned to be received within slot 542B of jaw element 512B, as illustrated in FIG. 14. First end 554B of latch element 552B is pivotally connected to jaw element 512B by a pivot pin 562B that extends through jaw element 512B perpendicular to the upper and lower surfaces of jaw element 512B. As illustrated in FIG. 14, pivot pin 562B has a length greater than the thickness of jaw element 512B, such that portions of pivot pin 562B extend beyond the upper surface of jaw element 512B and beyond the lower surface of jaw element 512B.

Second end 556B of latch element 552B is generally L-shaped and defines a finger 566B that extends to one side of latch element 552B. Between first and second ends 554B, 556B of latch element 552B, a contoured surface 572B is formed. Contoured surface 572B has a curved, circular shape dimensioned to engage a support 150 or 250, as shall be described in greater detail below. Between contoured surface 572B and second end 556B of latch element 552B, tab 574B extends to one side of latch element 552B. A notch is formed on the other edge of latch element 552B to form a projection 576B, best seen in FIG. 14.

Jaw/latch assembly 510B is designed to be disposed between inner plates 314, 316 of body section 310. The extending portions of pivot pin 562B are received within bored openings in inner plates 314, 316, as best seen in FIG. 17. Inner plates 314, 316 are formed to have recesses to receive jaw element 512B and to allow jaw element 512B to move about the axis of pivot pin 562B within the cavity defined between inner plates 314, 316 by the recesses therein.

A jaw-biasing element 582B is attached to jaw element 512B to bias jaw element 512B toward a "non-clamping position," as shall be described in greater detail below. In the embodiment shown, jaw-biasing element 582B is a tension spring that is attached at one end to one edge of jaw element 512B, as best seen in FIGS. 4-8. The other end of biasing element 582B is attached to a pin 584B extending between inner plates 314, 316. In the embodiment shown, jaw-biasing element 582B biases cam roller 516B on jaw element 512B toward shaft 412 of handle/actuator assembly 410, as will be discussed in greater detail below. A latch-biasing element 592B is attached to latch element 552B. One end of latch-biasing element 592B is mounted to projection 576B on latch element 552B, and a second end of latch-biasing element 592B is mounted to a pin 594B that extends between inner plates 314, 316, as best seen in FIGS. 4-8. Latch-biasing element 592B is dimensioned to bias latch element 552B in a direction away from shaft 412 of handle/actuator assembly 410. Latch-biasing element 592B and pin 594B are disposed within a slot or groove 382 formed in the inner surface of inner plates 314, 316, as best seen in FIGS. 4-8. Each slot or groove 382 communicates with a central cavity 384 and defines a shoulder surface 386. A compression spring 598B is disposed on the opposite side of latch element 552B, in general alignment with latch-biasing element 592B. In this respect, compression spring 598B is basically axially aligned with latch-biasing element 592B.

As indicated above, handle/actuator assembly 410 and jaw/latch assemblies 510A, 510B are dimensioned to be captured between inner plates 314, 316 within the cavities formed along inner surfaces 314a, 316a thereof. As best seen in FIG. 4, shaft 412 of handle/actuator assembly 410 defines a central axis "X" that extends through body section 310 of transfer device 300. Jaw/latch assembly 510A is disposed to one side of handle/actuator assembly 410, and jaw/latch assembly 510B is disposed on the opposite side of handle/actuator assembly 410. In this respect, respective jaw/latch assemblies 510A, 510B are symmetrical with respect to axis "X" of the shaft 412 of handle/actuator assembly 410. Jaw/latch assemblies, 510A, 510B are respectively movable about pivot pins 562A, 562B. Jaw elements 512A, 512B are dimensioned such that rollers 516A, 516B operatively engage cam surface 424 of actuator 422, as shown in FIGS. 9-12.

As best seen in FIG. 4, cam surface 424 of actuator 422 is rounded, so as to allow rollers 516A, 516B to roll therealong, as jaw elements 512A, 512B pivot about pivot pins 562A, 562B. Jaw-biasing elements 582A, 582B, i.e., the tension springs, are operatively disposed so as to bias rollers 516A, 516B on jaw elements 512A, 512B, respectively, toward cam actuator 422. In other words, jaw-biasing elements 582A, 582B bias rollers 516A, 516B on jaw elements 512A, 512B into engagement with cam surface 424 of actuator 422. With reference to FIG. 4, jaw-biasing element 582A, i.e., attached to jaw/latch assembly 510A, biases jaw element 512A in a clockwise direction, and jaw-biasing element 582B, attached to jaw/latch assembly 510B, biases the associated jaw element 512B in a counter-clockwise direction.

As illustrated in FIGS. 4-8, latch elements 552A, 552B of jaw/latch assemblies 510A, 510B are biased by latch-biasing elements 592A, 592B in an outward direction, i.e., away from shaft 412 of handle/actuator assembly 410. When in an outermost position, latch element 552A extends into support-receiving recess 320A and latch element 552B extends into support-receiving recess 320B of housing body 310, wherein contoured-surfaces 572A, 572B extend into a respective support-receiving opening 320A, 320B. As illustrated in FIG. 4, when latch element 552B of jaw/latch assembly 510B is in this position, compression spring 598B does not engage latch element 552B.

As will be described in greater detail below, a latch element 552A, 552B can assume its outermost position (shown in FIG. 4 with respect to latch element 552B) only when handlebar 472 of handle/actuator assembly 410 is in a generally horizontal position, as illustrated in FIG. 3. In this position, handlebar 472 of handle/actuator assembly 410 is aligned along the parting plane defined by inner plates 314, 316. In this respect, intermediate plate 452 of handle/actuator assembly 410 is positioned wherein slots 456 in the cylindrical wall portion 452b of intermediate plate 452 align with the plane through which latch elements 552A, 552B move. As a result, fingers 566A, 566B at second ends 556A, 556B of latch elements 552A, 552B can move through slots 456 in cylindrical wall portion 452b of intermediate plate 452. FIG. 4 shows finger 566B of latch element 552B of jaw/latch assembly 510B disposed within slot 456 in cylindrical wall portion 452b of handle/actuator assembly 410. In this position, latch element 552B is in its outermost position away from axis "X" of handle/actuator assembly 410. The force exerted by latch-biasing elements 592A, 592B cause the outer edges of latch elements 552A, 552B to abut shoulder 386 defined in inner plates 314, 316, as shown in FIG. 4.

The range of motion of latch elements 552A, 552B is illustrated in FIG. 4, wherein latch element 552A of jaw/latch assembly 510A is shown in its innermost position and wherein latch element 552B of jaw/latch assembly 510B is shown in its outermost position. As shall be discussed in greater detail below, a latch element 552A or 552B is in its innermost position when a support 150 or 250 is clamped against it, and a latch element 552A or 552B is in its outermost position when latch element 552A or 552B abuts shoulder 386 in inner plates 314, 316.

Upper and lower housing 312, 318 and intermediate plates 314, 316 are dimensioned to be secured together, with handle/actuator assembly 410 and jaw/latch assemblies 510A, 510B disposed therebetween. As best illustrated in FIGS. 4-8 and 17, elongated fasteners 398 extend into lower housing 318, through intermediate plates 314, 316, and into upper housing 312 to secure the respective components together. The relative positions of fasteners 398 are shown in FIGS. 4-8.

Referring now to FIGS. 3 and 17, adapter section 610 is best seen. Adapter section 610 is attachable to body section 310 and is designed to support medical apparatus 20. In the embodiment shown, adapter section 610 includes an enlarged first end 612 having a flat end surface 612a. Enlarged end 612 is dimensioned to mate with the flat end of body section 310 and to be attached thereto by conventional fastener 614 extending through holes 616 in end 612 into body section 310.

Adapter 610 includes a beam-like, central body portion 622 that connects first end 612 to a second end 632 that is adapted to hold and support medical apparatus 20. In the embodiment shown, second end 632 of adapter section 610 is a tubular sleeve that is dimensioned to receive post 34 on support frame 22. A locking device, such as a set screw (not shown), can be provided in second end 632 to secure post 34 therein. As will be appreciated from a further reading of the specification, second end 632 of adapter section 610 may assume other configurations for holding medical apparatus 20.

Referring now to FIGS. 4-12, the present invention shall be further described with respect to the operation of transfer system 10 and transfer device 300. Transfer device 300 is designed to attach onto a support, such as supports 150, 250, and to be transferable from one support 150, 250 to another support 150, 250. Hereinafter, the support 150, 250 that is to receive transfer device 300 shall be referred to as "receiving-support," and the support that is to transfer and release transfer device 300 shall be referred to as "transferring-support."

As will be appreciated from a reading of the following, the transferring-support 150, 250 may be on a stationary support assembly 100 or a vehicle support assembly 200, and the receiving support 150, 250 may be on a stationary support assembly 100 or a vehicle support assembly 200. In other words, transfer device 300 may be moved between a stationary support assembly 100 and a vehicle support assembly 200 and vice-a-versa, or between two stationary support assemblies 100 or two vehicle support assemblies 200.

As shall be described in greater detail below, transfer device 300 includes certain safety features that permit the transfer of transfer device 300 from one support 150, 250 to another support 150, 250 only when a receiving-support 150, 250 is of a proper size. Further, transfer of transfer device 300 from a transferring-support 150, 250 to a receiving-support 150, 250 will occur only when transfer device 300 is securely affixed, i.e., clamped, to the receiving-support 150, 250. Only then, will transfer device 300 release from, i.e., detach from, the releasing-support 150, 250.

Still further, rotation of handle/actuator assembly 410 to initiate transfer of transfer device 300 from a transferring-support 150, 250 to a receiving-support 150, 250 is permitted only when the receiving-support 150, 250 is disposed within a receiving opening 320A, 320B of transfer device 300. Only then is rotation of handle/actuator assembly 410 possible.

The operation of transfer device 300 shall now be described with respect to the transfer of transfer device 300 from a transferring-support 150 of a stationary support assembly 100 to a receiving-support 250 of a vehicle-support assembly 200. As will be appreciated, since supports 150, 250 are both comprised of like-diameter, metallic tubes, the positions of the respective supports 150, 250 could be reversed without affecting the operation of transfer device 300 or the following description of the operation thereof.

Figure 9:
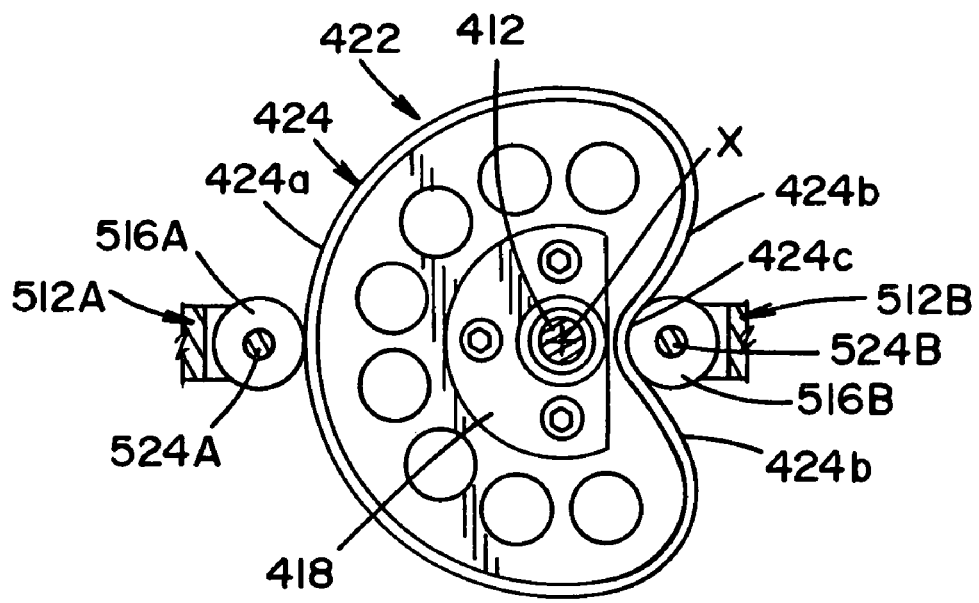
FIG. 9 is a sectional view taken along lines 9-9 of FIG. 4.

FIG. 4 shows transferring-support 150 clamped into receiving recess 320A of transfer device 300 by jaw element 512A. In FIG. 4, jaw element 512A is in a "clamped position" and jaw element 512B of jaw/latch assembly 510B is in a "non-clamping position." FIG. 9 shows the position of actuator 422, as viewed when looking along axis "X" of actuator shaft 412. As illustrated in FIG. 4, the transferring-support 150 is within support-receiving recess 320A of transfer device 300 and is held in position against the inner surface of the support-receiving recess 320A by jaw element 512B. FIG. 9 shows the position of actuator 422, when jaw element 512A of jaw/latch assembly 510A is in the "clamping position," as seen in FIG. 4. As seen in FIG. 9, roller 516A on jaw element 512A is forced outward, away from shaft 412. As a result, jaw face 514A of jaw element 512A is forced against transferring-support 150, thereby forcing transferring-support 150 against U-shaped guides 332 and pads 344 in support-receiving recess 320A. In other words, jaw element 512A of jaw/latch assembly 510A forces transferring-support 150 against guides 332 and U-shaped pads 344 mounted within upper and lower housing 312, 318.

As illustrated in FIG. 4, clamping of transferring-support 150 forces latch element 552A of jaw/latch assembly 510A against compression spring 598A to a position where end 556A of latch element 552A does not obstruct circular passages 362P, 364P formed in the end faces of inner plates 314, 316. As also shown in FIG. 4, latch element 552B of jaw/latch assembly 510B is in a position wherein end 556B of latch element 522B is disposed within slot 456 in cylindrical wall portion 452b of intermediate plate 452. In this position, latch element 552B prevents rotation of handle/actuator assembly 410, thereby preventing jaw element 512A of jaw/latch assembly 510 from moving and releasing transferring-support 150.

To transport transfer device 300 from support 150 to support 250 requires that support 250 be positioned within support-receiving recess 320B. Because support 150 is rotatable about its own axis, as illustrated in FIG. 1, support-receiving recess 320B may be repositioned by rotating transfer device 300 about the axis of support 150, thereby repositioning support-receiving recess 320B relative to support 250.

Figure 5:
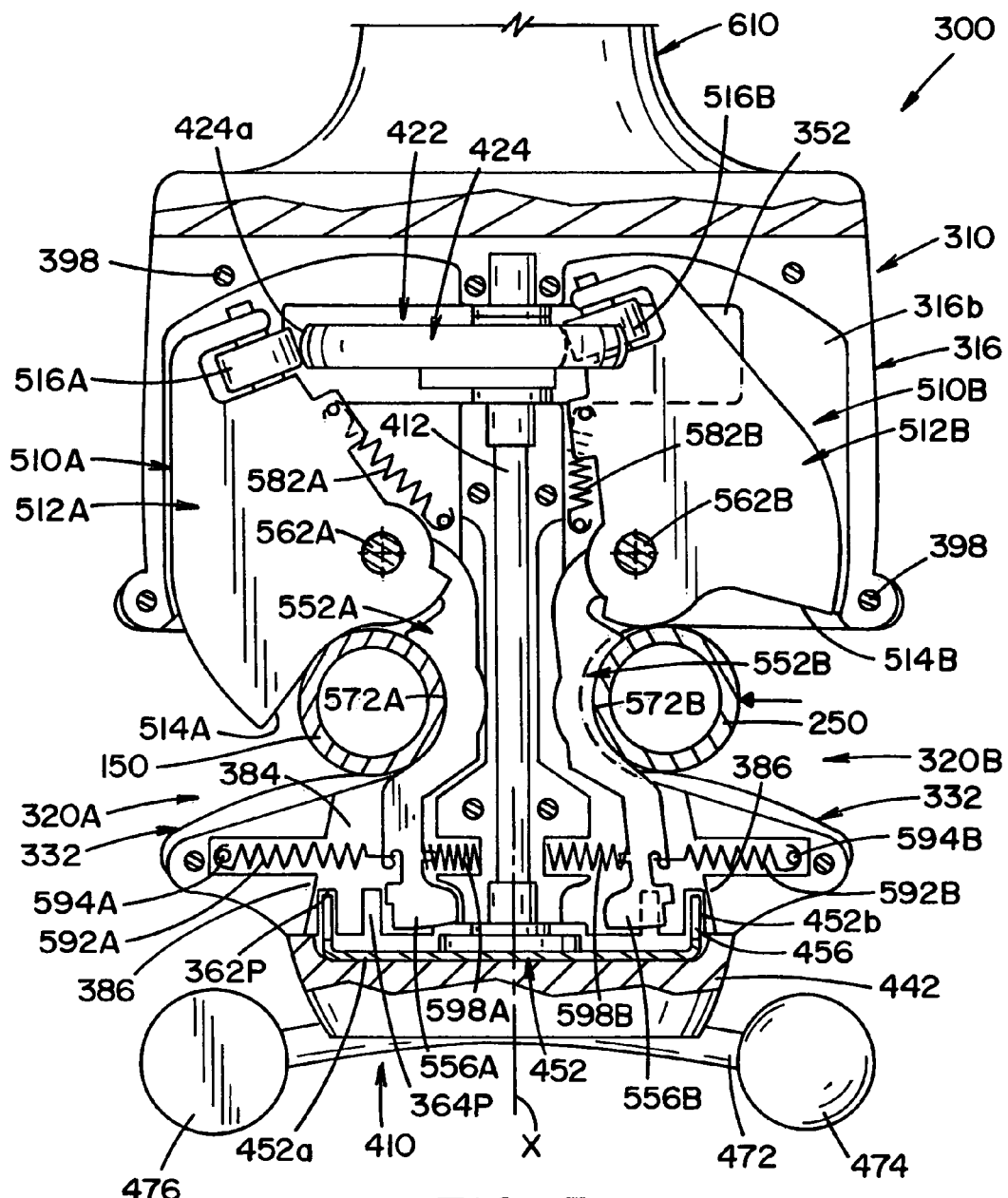
FIG. 5 is a sectional view similar to FIG. 4, showing the transfer device attached to a first support and a second support in a support-receiving position.

FIG. 5 illustrates the relative position of the internal components of transfer device 300 when receiving-support 250 is positioned in support-receiving recess 320B of transfer device 300. In this respect, transfer device 300 and receiving-support 250 are moved relative to each other to position receiving-support 250 within support-receiving recess 320B of transfer device 300. A slightly misaligned receiving-support 150, 250 can be inserted into support-receiving recess 320B, as guides 332 at the upper and lower ends of support-receiving recess 320B help align receiving-support 150, 250 relative to support-receiving recess 320B. As illustrated in FIG. 5, as receiving-support 250 enters the support-receiving recess 320B, it causes latch element 552B to move toward actuator shaft 412. In other words, positioning of receiving-support 250 within support-receiving recess 320B provides sufficient force to overcome the biasing force exerted by latch-biasing element 592B on latch element 552B. As a result, latch element 552B will move toward shaft 412 of handle/actuator assembly 410 until the inner edge of latch element 552B contacts the compression spring 598B. Compression spring 598B is dimensioned to require a significant amount of force to compress compression spring 598B. In other words, the opposing force of compression spring 598B will not be overcome by mere contact or engagement between receiving-support 250 and latch element 552B. As illustrated in FIG. 5, latch element 552B has moved sufficiently to cause end 556B of latch element 552B to move out from slot 456 in cylindrical wall portion 452b of intermediate plate 452. Removal of end 556B of latch element 552B from slot 456 in cylindrical wall portion 452b allows rotation of handle/actuator assembly 410 about axis "X."

Figure 6:
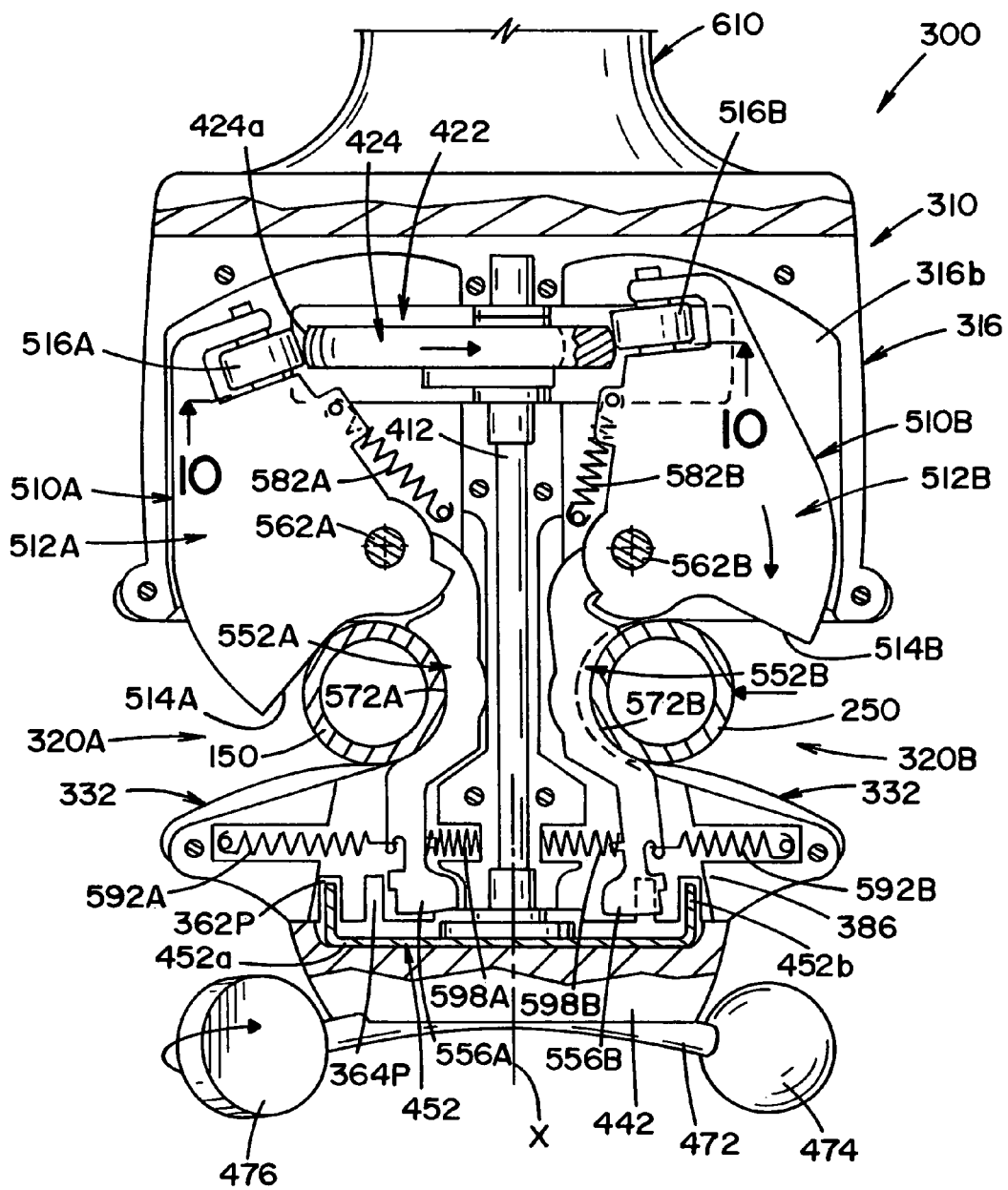
FIG. 6 is a sectional view similar to FIG. 5, showing an initial phase of a transfer procedure for attaching the transfer device to the second support.
Figure 10:
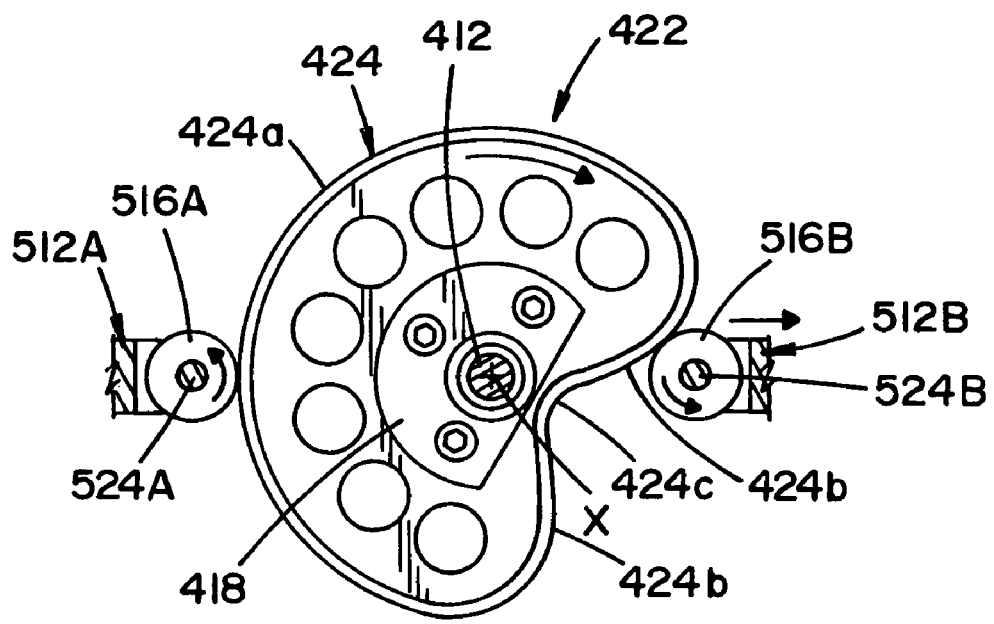
FIG. 10 is a sectional view taken along lines 10-10 of FIG. 6.

With receiving-support 250 within support-receiving recess 320B, and with latch element 552B moved out of slot 456 in intermediate plate 452, rotation of handle/actuator assembly 410 is allowed. FIG. 6 illustrates the position of the internal components of transfer device 300 during rotation of handle/actuator assembly 410 from the initial position shown in FIG. 4. Rotation of handle/actuator assembly 410 in a clockwise direction causes actuator 422 to move to a position as illustrated in FIG. 10. Rotation of actuator 422 causes jaw element 512B to pivot clockwise about pivot pin 562B, as roller 516B associated therewith rolls up along transition section 424b of cam surface 424. Jaw element 512A remains in a locked position as roller 516A associated therewith continues to roll along circular section 424a of cam surface 424. As illustrated in FIG. 6, latch element 552B remains essentially in the same position, with its inner edge against compression spring 598B.

Figure 7:
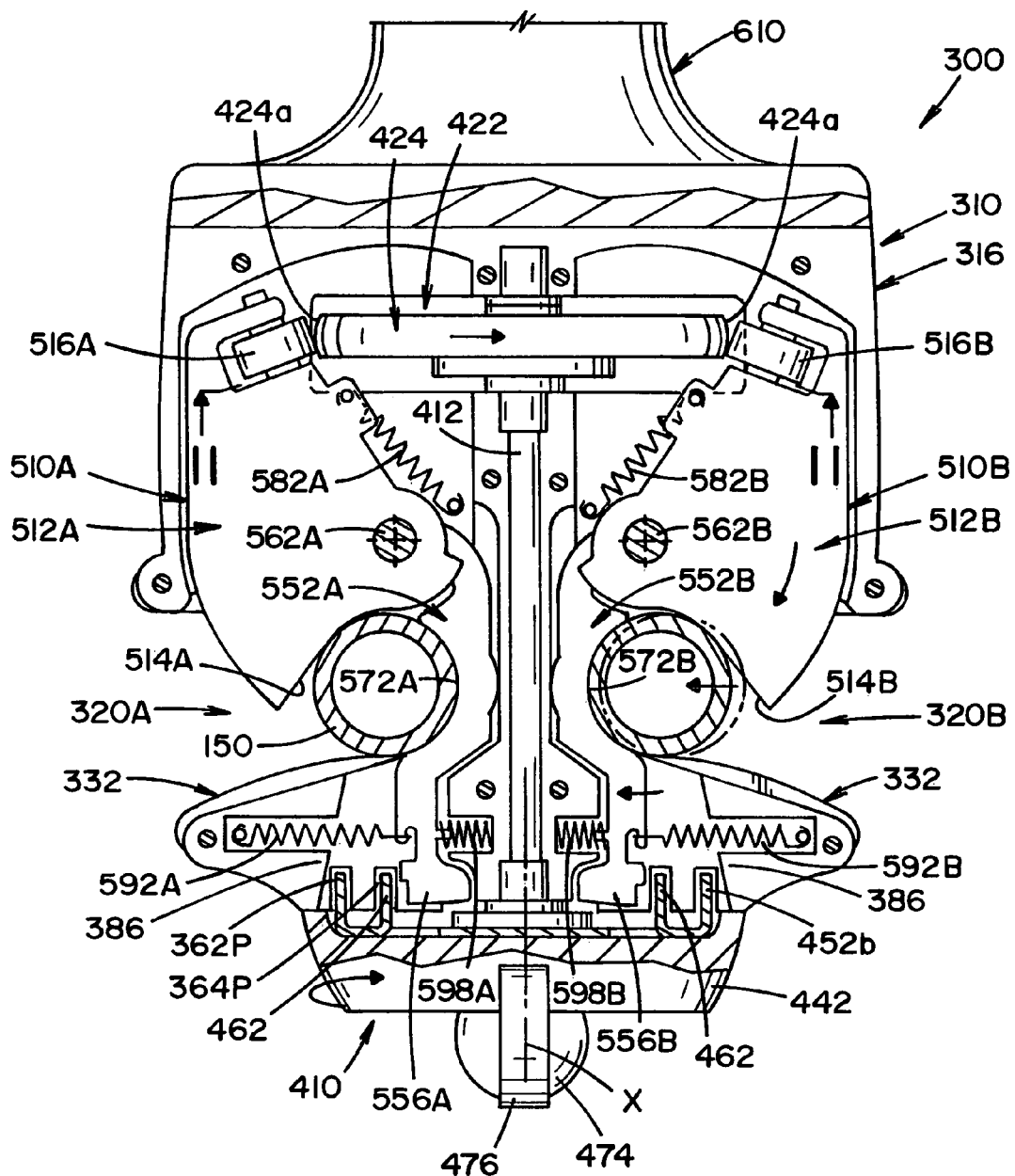
FIG. 7 is a sectional view similar to FIG. 6, showing the transfer device attached to both supports.
Figure 11:
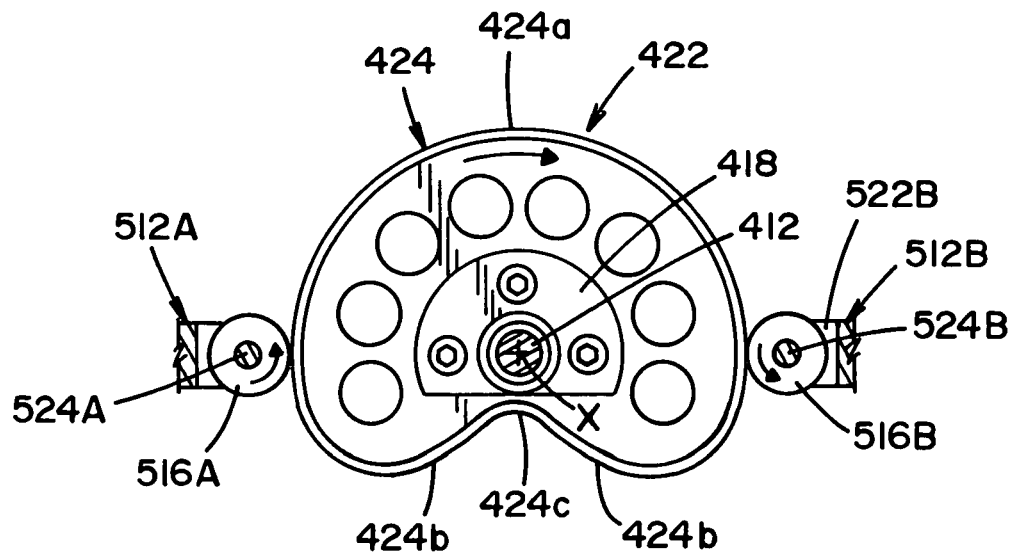
FIG. 11 is a sectional view taken along lines 11-11 of FIG. 7.

Referring now to FIGS. 7 and 11, as handle/actuator assembly 410 continues to rotate in a clockwise direction, actuator 422 will reach a position as shown in FIG. 11. In this position, both rollers 516A, 516B ride, i.e., are disposed on circular section 424a of cam surface 424 of actuator 422. As illustrated in FIG. 7, jaw element 512B now engages receiving-support 250 and forces receiving-support 250 against the contoured surface 572B of latch element 552B. Through the mechanical advantage gained by the arrangement of cam surface 424 and roller 516B, jaw element 512B forces receiving-support 250 against latch element 552B with sufficient force to compress compression spring 598B. In other words, the mechanical advantage gained by the arrangement of cam surface 424 and roller 516B, in addition to the mechanical advantage determined by the geometry of jaw 512B, the location of pivot pin 562B, and the location of roller 516B, provides sufficient force to cause receiving-support 250 to force latch element 552B against compression spring 598B and overcome the compressive force thereof. As illustrated in FIG. 7, in this position, end 556B of latch element 552B has moved to its innermost position. In this position, end 556B of latch element 552B no longer obstructs inner circular passage 364P formed on the end faces of inner plates 314, 316. As a result, handle/actuator assembly 410 is allowed to rotate further and tabs 462 that extend from the inner surface of intermediate plate 452 are allowed to pass through inner circular passage 364P formed along the end faces of inner plates 314, 316.

Each latch element 552A, 552B basically defines a locking element that controls movement, i.e., rotation of handlebar 472, and, in turn, controls movement of actuator 422. In the embodiment shown, each latch element 552A, 552B defines a locking element having three positions. Using latch element 552B as an example, in a first position, shown in FIG. 4, latch element 552B acts as a locking element to prevent movement of handlebar 472 and actuator 422.

In a second position, shown in FIG. 6, latch element 552B acts as a locking element and allows limited movement of handlebar 472 and actuator 422. In the second position, latch element 552B allows sufficient movement of actuator 422 to move both jaw elements 512A, 512B to a clamping position, but prevents further movement that would complete the transfer of transfer device 300 from transferring-support 150 to receiving-support 250.

In a third position, shown in FIG. 7, latch element 552B is in a position allowing complete rotation of handlebar 472 and movement of actuator 422 to allow actuator 422 to move from a first actuator position (shown in FIG. 9) to a second actuator position (shown in FIG. 12). When actuator 422 is in its first actuator position, transfer device 300 is attached to a first support, i.e., transferring-support 150. When actuator 422 is in its second actuator position, transfer device 300 is attached to a second support, i.e., receiving-support 250. In the embodiment shown, when handlebar 472 moves 180 angular degrees, actuator 422 moves from a first actuator position to a second actuator position. Depending upon the position of handlebar 472 and actuator 422, transfer device 300 is attached to one support 150 or 250, and the other support is released. Transfer device 300 preferably includes position detents (not shown) to identify when handlebar 472 is in the positions shown in FIGS. 4 and 8.

Figure 8:
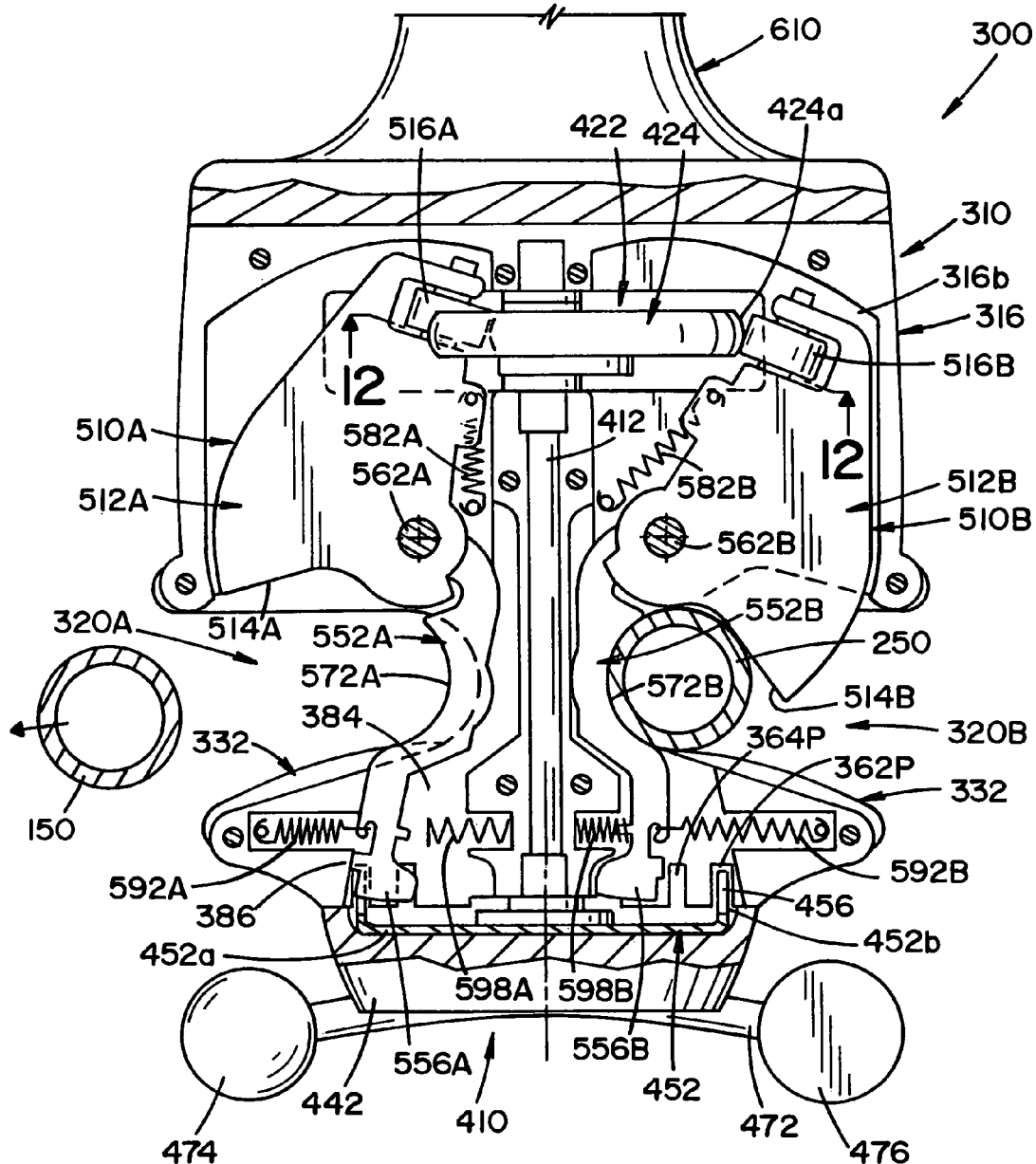
FIG. 8 is a sectional view similar to FIG. 7, showing the transfer device attached to the second support and the first support being released from the transfer device.

With jaw element 512B forcing receiving-support 250 against latch element 552B, latch element 552B will move sufficiently to allow further rotation of handle/actuator assembly 410. FIGS. 8 and 12 show the relative position of handle/actuator assembly 410 and actuator 422 upon completion of a 180° rotation of handlebar 472. As illustrated in FIG. 12, roller 516B associated with jaw element 512B is disposed along circular section 424a of cam surface 424, thereby maintaining jaw element 512B in a clamped position against receiving-support 250. As also shown in FIG. 12, roller 516A associated with jaw element 512A has moved into position within valley section 424c of cam surface 424. In this position, jaw-biasing element 582A connected to jaw element 512A rotates jaw element 512A in a clockwise direction about pivot pin 562A, thereby releasing transferring-support 150. Latch element 552A associated with jaw/latch assembly 510A has moved to its outermost position, away from the central axis of shaft 412. In this position, end 556A of latch element 552A is disposed within slot 456 in cylindrical wall portion 452b of intermediate plate 452, thereby preventing further rotation of handle/actuator assembly 410. Thus, receiving-support 250 is firmly clamped within the transfer device 300. Transfer device 300 and any associated medical apparatus 20 mounted thereto are now fixed to receiving-support 250 and supported thereby. As indicated by the foregoing, a transfer of transfer device 300 from a transfer-support 150, 250 to a receiving-support 150, 250 cannot occur until transfer device 300 is fixedly attached, i.e., clamped onto, the receiving-support 150, 250.

Transfer device 300 is designed so as not to be rotationally movable relative to support 250. However, as indicated above, support 250 is rotatable about its vertical axis relative to bracket 232 and bed 212. Accordingly, transfer device 300 and support 250 may be rotated about the axis of support 250, to move transfer device 300 and the medical apparatus 20 mounted thereto to various positions about the corner of bed 212. In other words, medical apparatus 20 is generally movable along a circular path having the axis of support 250 as a center point. In a similar fashion, when transfer device 300 is mounted to support 150, apparatus 20 that is mounted on transfer device 300, is movable along a circular path about the axis of support 150.

The configuration of transfer device 300 provides a safety mechanism in the event that an attempt is made to attach transfer device 300 to an improperly-sized support. In this respect, if the support to receive transfer device 300 is too small, clamping of the smaller support will not move latch element 552A or 552B sufficiently to cause ends 556A or 556B of latch element 552A or 552B to clear inner passage 364P formed in the end faces of inner plates 314, 316. As a result, tabs 462 on intermediate plate 452 will not be allowed to rotate through inner circular passage 364P, thus preventing further rotation of handle/actuator assembly 410. With further rotation prevented, actuator 422 remains in position as shown in FIG. 11, where both jaw element 512A and jaw element 512B are in a clamped position.

If an attempt is made to attach transfer device 300 to an oversized support, transfer of transfer device 300 to such a support will, likewise, be prevented. In this respect, an oversized support, i.e., a support having a larger diameter, will not be received by guides 332 that are located at the upper and lower ends of the support-receiving recesses 320A, 320B. FIG. 16B illustrates an oversized support, designated 750, disposed with support-receiving recess 320A. As shown in the drawings, guides 332 have spaced-apart arms 332a, 332b that define a predetermined width for elongated recess 320A. The spacing between arms 332a, 332b of guides 332 limits the size of a support that can be inserted therein. Only a support of the proper diameter (or smaller) will be received in the support-receiving recesses 320A, 320B, as illustrated in FIG. 16A. Larger-diameter supports are prevented by guides 332 from entering support-receiving recesses 320A, 320B. As a result, the necessary movement of latch element 552A is prevented, and handlebar 472 cannot be moved from its initial position, as illustrated in FIG. 4.

The foregoing structure thus prevents an improperly-sized support from being used in transfer device 300. As will be appreciated, an improperly-sized support, i.e., one of smaller diameter, would reduce the clamping force of jaw element 512A or 512B against a support disposed within the support-receiving recesses 320A or 320B.

Transfer device 300 thus provides for transfer of medical apparatus 20 from transferring-support 150 to receiving-support 250, and vice-a-versa. As will be noted, vertical repositioning of transfer device 300 is not required to move transfer device 300 from one support to another. In this respect, transfer device 300 is movable in a generally horizontal direction, maintaining the same vertical position, i.e., height, when transferred from one support to another. In addition, as will be noted, in the embodiment shown, transfer device 300 is attachable anywhere along the lengths of supports 150, 250. Thus, vertical repositioning of supports 150, 250 is likewise not required. As indicated above, support 150, 250 may be part of a stationary support assembly 100 or a vehicle-support assembly 200.

The present invention thus provides a transfer device 300 for the horizontal transfer of medical apparatus 20 from one support 150, 250 to another support 150, 250. Transfer device 300 includes safety features that prevent accidental release of transfer device 300 from a support 150, 250 and further prevent an undersized or oversized support from being inserted into transfer device 300.

The foregoing description is a specific embodiment of the present invention. It should be appreciated that this embodiment is described for purposes of illustration only, and that numerous alterations and modifications may be practiced by those skilled in the art without departing from the spirit and scope of the invention. While system 100 and transfer device 300 have been described with respect to a medical environment, the present invention is not limited to such application. It is intended that all such modifications and alterations be included insofar as they come within the scope of the invention as claimed or the equivalents thereof.

Having described the invention, the following is claimed:

1. A transfer device transferable from one support to another support, said transfer device comprised of:
   a housing having first and second support-receiving recesses, each recess dimensioned to receive a support therein;
   a first clamping element mounted to said housing, said first clamping element being associated with said first recess and being movable relative thereto between a support-clamping position wherein said clamping element captures said support in said first recess and a release position wherein said support is movable into and out of said first recess;
   a second clamping element mounted to said housing, said second clamping element being associated with said second recess and being movable relative thereto between a support-clamping position wherein said clamping element captures said support in said second recess and a release position wherein said support is movable into and out of said second recess;
   an actuator connected to said first and second clamping elements for moving each of said clamping elements between said support-clamping position and said release position, wherein said first clamping element is in a support clamping position and said second clamping element is in a release position when said actuator is in a first position, and said second clamping element is in a support clamping position and said first clamping element is in a release position when said actuator is in a second position.

2. A transfer device as defined in claim 1, wherein said first clamping element is rotatable about a first axis through said housing and said second clamping element is rotatable about a second axis through said housing.

3. A transfer device as defined in claim 2, wherein said first axis is parallel to said second axis.

4. A transfer device as defined in claim 1, wherein said device supports an apparatus, and is movable between said first support and said second support.

5. A transfer device as defined in claim 4, wherein said apparatus is a medical device.

6. A transfer device as defined in claim 1, wherein said supports are cylindrical in shape.

7. A transfer device as defined in claim 6, wherein said supports are metallic tubes.

8. A transfer device as defined in claim 6, wherein said supports are rods formed of a reinforced polymer.

9. A transfer device as defined in claim 1, wherein said supports have a uniform cross-section along a linear axis.

10. A transfer device transferable from one support to another support, said transfer device comprised of:
    a housing having first and second support-receiving recesses, each recess dimensioned to receive a support therein;
    a first clamping element mounted to said housing, said first clamping element being associated with said first recess and being movable relative thereto between a support-clamping position wherein said clamping element captures said support in said first recess and a release position wherein said support is movable into and out of said first recess;
    a second clamping element mounted to said housing, said second clamping element being associated with said second recess and being movable relative thereto between a support-clamping position wherein said clamping element captures said support in said second recess and a release position wherein said support is movable into and out of said second recess; and
    an actuator connected to said first and second clamping elements for moving each of said clamping elements between said support-clamping position and said release position, wherein said actuator is a rotatable cam and said first and second clamping elements each include a roller thereon that engages said cam.

11. A transfer device transferable from one support to another support, said transfer device comprised of:

a housing having first and second support-receiving recesses, each recess dimensioned to receive a support therein;

a first clamping element mounted to said housing, said first clamping element being associated with said first recess and being movable relative thereto between a support-clamping position wherein said clamping element captures said support in said first recess and a release position wherein said support is movable into and out of said first recess;

a second clamping element mounted to said housing, said second clamping element being associated with said second recess and being movable relative thereto between a support-clamping position wherein said clamping element captures said support in said second recess and a release position wherein said support is movable into and out of said second recess; and an actuator connected to said first and second clamping elements for moving each of said clamping elements between said support-clamping position and said release position; and a control handle that is rotatable about a handle axis through said housing, said control handle being connected to said actuator to cause said actuator to move between first and second actuator positions, wherein said first clamping element is in a support clamping position and said second clamping element is in a release position when said actuator is in said first actuator position, and said second clamping element is in a support clamping position and said first clamping element is in a release position when said actuator is in said second actuator position.

12. A transfer device as defined in claim 11, wherein said first clamping element is in said support-clamping position and said second clamping element is in said release position when said handle is in a first position and said first clamping element is in said release position and said second clamping element is in said support-clamping position when said handle is in a second position.

13. A transfer device as defined in claim 12, further comprising a latch assembly preventing rotation of said handle, unless a support is disposed in each of said first and second recesses.

14. A transfer device transferable from one support to another support, said transfer device comprised of:

a housing having first and second support-receiving recesses, each recess dimensioned to receive a support therein;

a first clamping element mounted to said housing, said first clamping element being associated with said first recess and being movable relative thereto between a support-clamping position wherein said clamping element captures said support in said first recess and a release position wherein said support is movable into and out of said first recess;

a second clamping element mounted to said housing, said second clamping element being associated with said second recess and being movable relative thereto between a support-clamping position wherein said clamping element captures said support in said second recess and a release position wherein said support is movable into and out of said second recess; and an actuator connected to said first and second clamping elements for moving each of said clamping elements between said support-clamping position and said release position, wherein said actuator is movable between a first actuator position and a second actuator position, said first clamping element being in said support-clamping position when said actuator is in said first actuator position and being in said release position when said actuator is in said second actuator position, and said second clamping element being in said release position when said actuator is in said first actuator position and being in said support-clamping position when said actuator is in said second actuator position.

15. A transfer device as defined in claim 14, wherein another of said clamping elements is in said release position when said actuator is in said first actuator position and is in said support-clamping position when said actuator is in said second actuator position.

16. A transfer device as defined in claim 14 or 15, further comprising a locking element, said locking element having:

a first position preventing movement of said actuator;

a second position allowing limited movement of said actuator between said first and second actuator positions; and a third position allowing full movement of said actuator between said first and second actuator position.

17. A transfer device as defined in claim 16, further comprising a first biasing element biasing said locking element toward said first position.

18. A transfer device as defined in claim 17, wherein said biasing element is a tension spring.

19. A transfer device as defined in claim 16, further comprising a second biasing element biasing said locking element away from said third position.

20. A transfer device as defined in claim 19, wherein said second biasing element is a compression spring.

21. A transfer device as defined in claim 20, wherein said locking element moves from said first position to said second position when a support is disposed in a support-receiving recess.

22. A transfer device as defined in claim 21, wherein said locking element moves from said second position to said third position as a support is being captured by a clamping element moving from said release position to said support-clamping position.

23. A device transferable between one support and another support, said device comprised of:

a housing;

first and second movable clamping elements mounted to said housing, each of said clamping elements being movable between a support-clamping position and a support-release position;

a movable actuator connected to said first and second clamping elements, said actuator movable between a first actuator position and a second actuator position and operable to move each of said clamping elements between said support-clamping position and said support-release position;

a locking element connected to said actuator, said locking element having:

a first position preventing movement of said actuator;

a second position allowing limited movement of said actuator between said first and second actuator positions;

a third position allowing full movement of said actuator between said first and second actuator positions, wherein said actuator is a rotatable cam and said first and second clamping elements each include a roller thereon that engages said cam.

24. A device as defined in claim 23, wherein said actuator is movable between a first actuator position and a second actuator position, one of said clamping elements being in said support-clamping position when said actuator is in said first actuator position and being in said release position when said actuator is in said second actuator position.

25. A device as defined in claim 24, wherein another of said clamping elements is in said release position when said actuator is in said first actuator position and is in said support-clamping position when said actuator is in said second actuator position.

26. A device as defined in claim 23, further comprising a control handle that is rotatable about a handle axis through said housing, said control handle being connected to said actuator to cause said actuator to move between said first and second actuator positions.

27. A device as defined in claim 26, wherein said actuator is a rotatable cam and is connected to said handle by a shaft, said cam being rotatable about said handle axis.

28. A transfer device for transferring an apparatus from one support to another support, said transfer device comprising:
- a housing;
- two movable clamping elements mounted to said housing; each of said clamping elements being movable between a support-clamping position and a release non-clamping position;
- an actuator in operative engagement with said two clamping elements to move each of said clamping elements between said support-clamping position and said release position, said actuator having a first actuator position wherein one of said clamping elements is in said support-clamping position and another of said clamping elements is in said release position, and a second position wherein said one of said clamping elements is in said release position and said another of said clamping elements is in said support-clamping position.

29. A transfer device as defined in claim 28, further comprising a latch element associated with each of said clamping elements, said latch element having:
- a first position preventing movement of said actuator;
- a second position allowing limited movement of said actuator between said first and second actuator positions; and
- a third position allowing full movement of said actuator between said first and second actuator position.

30. A transfer device as defined in claim 29, further comprising a first biasing element biasing said locking element toward said first position.

31. A transfer device as defined in claim 30, wherein said biasing element is a tension spring.

32. A transfer device as defined in claim 29 further comprising a second biasing element biasing said locking element away from said third position.

33. A transfer device as defined in claim 32 wherein said second biasing element is a compression spring.

34. A transfer device as defined in claim 28, wherein said actuator is a cam rotatable about an axis.

35. A transfer device as defined in claim 34, further comprising a control handle movable about said axis, said control handle connected to said actuator to cause said actuator to move between said first and said second actuator positions.

36. A transfer system, comprised of:
- a plurality of parallel supports, each of said supports having areas of like cross-sectional shapes; and
- a device alternately attachable to one of said supports, said device having two jaws that are each movable between a support clamping position, wherein said jaw captures a support in said device and a release, non-clamping position, one of said jaws being in said clamping position attaching said device to one of said plurality of supports when the other of said jaws is in a release, non-clamping position, an actuator connected to each of said jaws, said actuator being movable between two positions, wherein movement of said actuator from one of said two positions to another of said two positions causes said one of said jaws to move from said clamping position to said release, non-clamping position and said other jaw to move to said clamping position.

37. A transfer system as defined in claim 36, further comprising a locking assembly preventing movement of said jaws unless a support is disposed in a clamping position relative to each of said jaws.

38. A transfer system as defined in claim 37, wherein said locking assembly includes a locking element associated with each of said jaws.

39. A transfer system, comprised of:
- a plurality of supports, each of said supports having areas of like cross-sectional shapes; and
- a device alternately attachable to one of said supports, said device having two jaws that are each movable between a support clamping position, wherein said jaw captures a support in said device and a release, non-clamping position, one of said jaws being in said clamping position attaching said device to one of said plurality of supports when the other of said jaws being in a release, non-clamping position, wherein said one of said jaws is movable from said clamping position to said release, non-clamping position when said other jaw moves to said clamping position, and wherein said device includes an actuator connected to each of said jaws, said actuator being movable between a first actuator position and a second actuator position, said one of said jaws being in said clamping position and said other of said jaws being in said release, non-clamping position when said actuator is in said first actuator position, and said one of said jaws being in said non-clamping and said other of said jaws being in said clamping position when said actuator is in said second actuator position.

40. A transfer system as defined in claim 39, wherein said actuator is a cam rotatable about an axis.

41. A transfer system as defined in claim 40, wherein said actuator is connected to a handle that is rotatable about said axis.

42. A transfer system as defined in claim 39, wherein said supports have a uniform cross-section along a linear axis.

43. A transfer system as defined in claim 42, wherein said supports have a circular cross-section.

44. A transfer system as defined in claim 43, wherein said supports are elongated tubes.

45. A transfer system as defined in claim 43, wherein said supports are formed of a material selected from the group consisting of metals, polymers, and fiber-reinforced polymers.

46. A transfer system, comprised of:
- a plurality of supports, each of said supports having areas of like cross-sectional shapes;
- a device alternately attachable to one of said supports, said device having two jaws that are each movable between a support clamping position, wherein said jaw captures a support in said device and a release, non-clamping position, one of said jaws being in said clamping position attaching said device to one of said plurality of supports when the other of said jaws being in a release, non-clamping position, wherein said one of said jaws is movable from said clamping position to said release, non-clamping position when said other jaw moves to said clamping position;

an actuator connected to said jaws for controlling movement thereof;

a locking assembly preventing movement of said jaws unless a support is disposed in a clamping position relative to each of said jaws, wherein said locking assembly includes a locking element associated with each of said jaws, and wherein each of said locking elements has:

a first position preventing movement of said actuator;

a second position allowing limited movement of said actuator between said first and second actuator positions; and a third position allowing full movement of said actuator between said first and second actuator position.

47. A transfer system as defined in claim 46, said locking element is disposed to contact a support when a support is in a clamping position, and said locking element moves from said first position to said second position when a support is in said clamping position.

48. A transfer system as defined in claim 47, wherein said locking element moves from said second position to said third position as a support is clamped by one of said two jaws.

* * * * *